(12) United States Patent
Fish et al.

(10) Patent No.: US 8,969,016 B2
(45) Date of Patent: Mar. 3, 2015

(54) RESONANCE ENERGY TRANSFER ASSAY WITH CLEAVAGE SEQUENCE AND SPACER

(71) Applicant: Biosentinel, Inc., Del Mar, CA (US)

(72) Inventors: Robert D. Fish, Tustin, CA (US); Min Dong, Madison, WI (US)

(73) Assignee: Biomadison, Inc., Del Mar, CA (US)

( * ) Notice: Subject to any disclaimer, the term of this patent is extended or adjusted under 35 U.S.C. 154(b) by 0 days.

(21) Appl. No.: 13/625,723

(22) Filed: Sep. 24, 2012

(65) Prior Publication Data

US 2013/0095513 A1    Apr. 18, 2013

Related U.S. Application Data

(62) Division of application No. 12/059,570, filed on Mar. 31, 2008.

(60) Provisional application No. 60/972,673, filed on Sep. 14, 2004.

(51) Int. Cl.

| | |
|---|---|
| *G01N 33/53* | (2006.01) |
| *G01N 31/00* | (2006.01) |
| *C07K 19/00* | (2006.01) |
| *C12Q 1/37* | (2006.01) |
| *G01N 33/542* | (2006.01) |
| *G01N 33/94* | (2006.01) |

(52) U.S. Cl.
CPC . *C07K 19/00* (2013.01); *C12Q 1/37* (2013.01); *G01N 33/542* (2013.01); *G01N 33/9406* (2013.01)
USPC ........... 435/7.21; 435/7.1; 436/501; 436/518; 424/9.1; 424/130.1; 424/520; 422/430; 530/300; 530/350

(58) Field of Classification Search
CPC . C07K 2317/92; C12Q 1/37; A61K 2039/505
See application file for complete search history.

(56) References Cited

U.S. PATENT DOCUMENTS

| | | | |
|---|---|---|---|
| 5,965,699 A | 10/1999 | Schmidt et al. | |
| 5,981,200 A * | 11/1999 | Tsien et al. | ................ 435/7.4 |
| 6,504,006 B1 | 1/2003 | Shine et al. | |
| 7,183,066 B2 | 2/2007 | Fernandez-Salas et al. | |
| 2006/0134722 A1 * | 6/2006 | Chapman et al. | ............. 435/23 |
| 2006/0233836 A1 | 10/2006 | Kincaid et al. | |

FOREIGN PATENT DOCUMENTS

| | | | | |
|---|---|---|---|---|
| WO | WO 00/23463 | * | 4/2000 | ............... C07K 7/08 |
| WO | 2004/029576 | | 4/2004 | |
| WO | 2004/031773 | | 4/2004 | |

OTHER PUBLICATIONS

Min Dong et al., Using Fluorescent Sensors to Detect Botulinum Neurotoxin Activity in Vitro and in Living Cells, Applied Biological Sciences.

Dong et al., Structural Determinants of the Specificity for Synaptic Vesicle-associates Membrane Protein/Synaptobrevin of Tetanus and Botulinum Type B and G Neurotoxins, The Journal of Biological Chemistry.

* cited by examiner

*Primary Examiner* — Lisa Cook

(74) *Attorney, Agent, or Firm* — Fish & Tsang, LLP

(57) ABSTRACT

A molecular construct comprises a donor label, an acceptor label, a linker peptide disposed between the donor and the acceptor, the linker having a cleavage site sequence, and a spacer between at least one of (a) the donor and the cleavage site sequence and (b) the acceptor and the cleavage site sequence. Preferably, the construct is selected from the group consisting of CFP-(SGLRSRA)-SNAP-25-(SNS)-YFP, and CFP-(SGLRSRA)-synaptobrevin-(SNS)-YFP. In preferred embodiments, the linker peptide is a substrate of a *botulinum* neurotoxin selected from the group consisting of synaptobrevin (VAMP), syntaxin and SNAP-25, or a fragment thereof that can be recognized and cleaved by the *botulinum* neurotoxin. Advantageously, the spacer increases the electronic coupling between the donor label and the acceptor label relative to a corresponding construct without the spacer.

8 Claims, 11 Drawing Sheets

|         |        | 4 h    | 16 h  |
|---------|--------|--------|-------|
|         | BoNT/A | 15 pM  | 10 pM |
|         | BoNT/E | 20 pM  | 6 pM  |
| EC50:   |        |        |       |
|         | BoNT/B | 242 pM | 32 pM |
|         | BoNT/F | 207 pM | 98 pM |

A: BoNT/A(50 nM), 72 h vs CONTROL — CELL COUNT vs FRET RATIO (1.3, 1.5, 1.7, 1.9)

B: BoNT/B(30 nM), 72 h vs CONTROL — CELL COUNT vs FRET RATIO (1.1, 1.3, 1.5, 1.7, 1.9)

- 310: PROVIDING A CONSTRUCT OF CLAIM 1, WHEREIN A LINKER IS A SUBSTRATE PROTEIN OR A CLEAVABLE FRAGMENT THEREOF OF THE BOTULINUM NEUROTOXIN TO BE DETECTED
- 320: EXPOSING THE CONSTRUCT TO A SAMPLE SUSPECTED OF CONTAINING THE BOTULINUM NEUROTOXIN UNDER A CONDITION UNDER WHICH THE BOTULINUM NEUROTOXIN CLEAVES THE SUBSTRATE PROTEIN OR THE FRAGMENT THEREOF
- 330: DETECTING AND COMPARING A FRET SIGNAL BEFORE AND AFTER THE CONSTRUCT IS EXPOSED TO THE SAMPLE, WHEREIN A DECREASE IN FRET INDICATES THE PRESENCE OF BOTULINUM NEUROTOXIN IN THE SAMPLE.

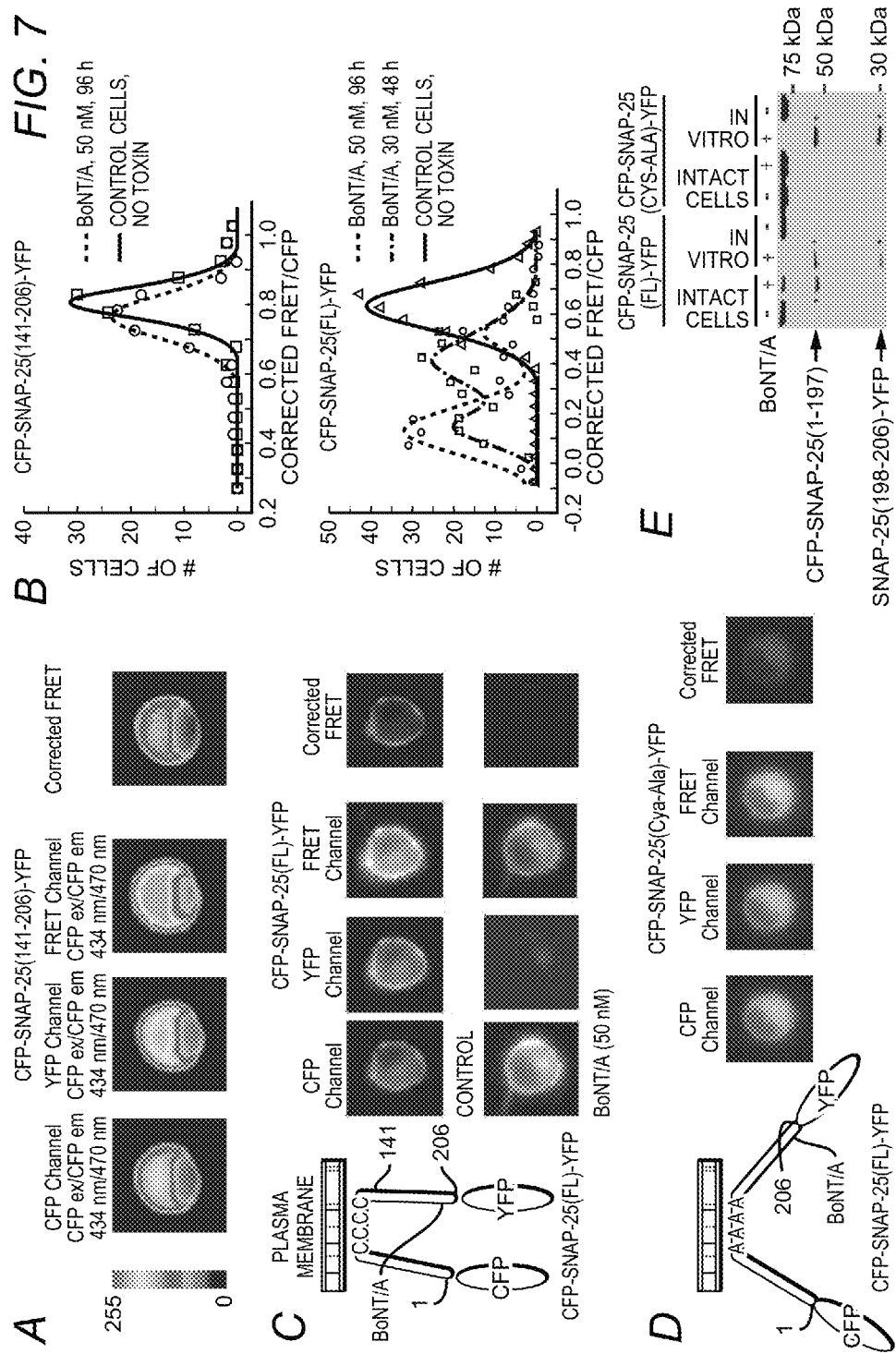

ent application Ser. No. 12/059,570 filed Mar. 31, 2008 which claims priority to U.S. Provisional application 60/972,673, filed Sep. 14, 2007 incorporated herein by reference in its entirety.

RESONANCE ENERGY TRANSFER ASSAY WITH CLEAVAGE SEQUENCE AND SPACER

This application is a divisional application of U.S. patent application Ser. No. 12/059,570 filed Mar. 31, 2008 which claims priority to U.S. Provisional application 60/972,673, filed Sep. 14, 2007 incorporated herein by reference in its entirety.

FIELD OF THE INVENTION

The field of the invention is fluorescence resonance energy transfer for protease assays related to *Botulinum* toxins and tetanus toxins.

BACKGROUND

*Botulinum* neurotoxins (BoNTs) are produced by *Clostridium botulinum* and are the most potent toxins known. These toxins are a well-recognized source of food poisoning, often resulting in serious harm or even death of the victims. There are seven structurally related *botulinum* neurotoxins or serotypes (BoNT/A-G), each of which is composed of a heavy chain (.about.100 KD) and a light chain (.about.50 KD). The heavy chain mediates toxin entry into a target cell through receptor-mediated endocytosis. Once internalized, the light chain is translocated from the endosomal vesicle lumen into the cytosol, and acts as a zinc-dependent protease to cleave proteins that mediate vesicle-target membrane fusion ("substrate proteins").

These BoNT substrate proteins include plasma membrane protein syntaxin, peripheral membrane protein SNAP-25, and a vesicle membrane protein synaptobrevin (Syb). These proteins are collectively referred to as the SNARE (soluble N-ethylmaleimide-sensitive factor attachment protein receptor) proteins. Cleavage of SNARE proteins blocks vesicle fusion with plasma membrane and abolishes neurotransmitter release at neuromuscular junction. Among the SNARE proteins, syntaxin and SNAP-25 usually reside on the target membrane and are thus referred to as t-SNAREs, while synaptobrevin is found exclusively with synaptic vesicles within the synapse and is called v-SNARE. Together, these three proteins form a complex that are thought to be the minimal machinery to mediate the fusion between vesicle membrane and plasma membrane. BoNT/A, E, and C.sup.1 cleave SNAP-25, BoNT/B, D, F, G cleave synaptobrevin (Syb), at single but different sites. BoNT/C also cleaves syntaxin in addition to SNAP-25.

Due to their threat as a source of food poisoning, and as bioterrorism weapons, there is a need to sensitively and speedily detect BoNTs. Currently, the most sensitive method to detect toxins is to perform toxicity assay in mice. This method requires large numbers of mice, is time-consuming and cannot be used to study toxin catalytic kinetics. A number of amplified immunoassay systems based on using antibodies against toxins have also been developed, but most of these systems require complicated and expensive amplification process, and cannot be used to study toxin catalytic activity either. Although HPLC and immunoassay can be used to detect cleaved substrate molecules and measure enzymatic activities of these toxins, these methods are generally time-consuming and complicated, some of them require specialized antibodies, making them inapplicable for large scale screening. Therefore, there is a need for new and improved methods and compositions for detecting BoNTs.

In FRET assays, two fluorigenic amino acid derivatives are used to replace two native amino acids in a very short synthetic peptide (20-35 amino acids) that contain toxin cleavage sites. The fluorescence signal of one amino acid derivative is quenched by another amino acid derivative when they are close to each other in the peptide, this mechanism is called "Förster resonance energy transfer" (FRET). Cleavage of the peptide separates the two amino acid derivatives and a decreases in FRET can be detected.

FRET assays have been successfully used for detecting BoNTs. (See e.g., US Pat. App. No. 2004/0191887 to Chapman, filed Oct. 28, 2003, US Pat. App. No. 2006/0134722 to Chapman, filed Dec. 20, 2004, U.S. Pat. No. 7,208,285 to Steward (April 2007), and U.S. Pat. No. 7,183,066 to Fernandez-Salas (February 2007), each of which is incorporated herein by reference in their entirety. Where a definition or use of a term in an incorporated reference is inconsistent or contrary to the definition of that term provided herein, the definition of that term provided herein applies and the definition of that term in the reference does not apply).

Although some success has been demonstrated in applying FRET assays to detection of BoNTs, the sensitivity and specificity are not sufficient. Improved apparatus, systems and methods are therefore needed.

SUMMARY OF THE INVENTION

The present invention provides apparatus, systems and methods in which a molecular construct comprises a donor label, an acceptor label, a linker peptide disposed between the donor and the acceptor, the linker having a cleavage site sequence, and a spacer between at least one of (a) the donor and the cleavage site sequence and (b) the acceptor and the cleavage site sequence.

In preferred embodiments the donor and the acceptor labels are positioned to provide an electronic coupling such that the donor label can transfer energy to the acceptor label by a dipole-dipole coupling mechanism. In especially preferred embodiments the dipole-dipole coupling mechanism is Förster resonance energy transfer (FRET).

The donor and the acceptor labels can be either a chromophore or a fluorophore moiety, wherein the emission spectrum of the donor label overlaps with the excitation spectrum of the acceptor label. Preferably, the donor is a green fluorescent protein or a variant thereof, and the acceptor is a corresponding variant of the green fluorescent protein. A particularly preferred donor and acceptor label (fluorophore pair) for the present invention is CFP-YFP.

In preferred embodiments, the linker peptide is a substrate of a *botulinum* neurotoxin selected from the group consisting of synaptobrevin (VAMP), syntaxin and SNAP-25, or a fragment thereof that can be recognized and cleaved by the *botulinum* neurotoxin ("cleavable fragment"). These proteins collectively are referred to as the SNARE (soluble n-ethylmaleimide-sensitive factor attachment protein receptor) proteins. The linker can have a primary structure length of any suitable length, including for example, greater than or equal to 5 nm, 8 nm, 10 nm, 12 nm, 14 nm, and 20 nm.

In especially preferred embodiments, the entire construct comprises CFP-(SGLRSRA)-SNAP-25-(SNS)-YFP, or CFP-(SGLRSRA)-synaptobrevin-(SNS)-YFP.

In one embodiment, the linker peptide comprises at least about 14 amino acid residues and an amino acid sequence selected from the group consisting of SEQ ID NOs: 1-6 (discussed infra). In a preferred embodiment, the linker peptide comprises at least about 15, or at least about 16, or at least about 17, or at least about 18, or at least about 19, or at least about 20, or at least about 21, or at least about 22, or at least about 23, or at least about 24, or at least about 25, or at least about 26, or at least about 27, or at least about 28, or at least about 29 amino acid residues, and a sequence is selected from the group consisting of SEQ ID NOs: 1-6 (discussed infra).

In a preferred embodiment, the linker peptide comprises at least about 30 amino acid residues and an amino acid sequence selected from the group consisting of SEQ ID NOs: 1-6. More preferably, the linker peptide comprises at least about 35 amino acid residues, or at least about 40 amino acid residues, or at least about 45 amino acid residues, or at least about 50 amino acid residues. In a particularly preferred embodiment, a construct of the present invention comprises a linker peptide that comprises at least about 55 amino acid residues, or at least about 65 amino acid residues.

The cleavage site sequence of the present invention can advantageously comprise (a) a SNARE protein, motif, mutein, and (b) a spacer with at least 5 amino acids, wherein the spacer includes a sequence selected from the group consisting of (GGGGS)n [Seq ID 7] and (EAAAK)n [Seq ID 8], where n is 1-3.

"Muteins" of a protein should be interpreted herein as having at least 30% identity with a corresponding native protein, including for example compositions having at least 35%, 40%, 45%, 50%, 55%, 60%, 65%, 70%, 75%, 80%, 85%, 90%, 95% or 98% identity with the native protein. Variations from identity can comprise any or more of additions, deletions and substitutions. Contemplated muteins include fragments, truncates and fusion proteins.

The spacer of the present invention can have any suitable number of amino acids, but preferably at least 3, 5, 7, 10, 12, or 15 amino acids. The spacer can include a sequence selected from the group consisting of (GGGGS)n [Seq ID 7] and (EAAAK)n [Seq ID 8], where n is 1-3. Alternatively, the spacer can comprise a SNARE motif. Advantageously, such configurations of the spacer increase the electronic coupling between the donor label and the acceptor label relative to a corresponding construct without the spacer.

The present invention further provides an isolated polynucleotide molecule encoding a construct described above. The construct is preferably an expression vector comprising the polynucleotide molecule operably linked to a promoter. A preferable promoter for the invention is an inducible promoter.

The present invention also provides a cell comprising an isolated polynucleotide molecule described above. In one embodiment, the cell is selected from the group consisting of a primary cultured neuron cell, PC12 cell or a derivative thereof, a primary cultured chromaphin cell, a neuroblastoma cell, a human adrenergic SK-N-SH cell, and a NS-26 cell line. Preferably, the cell is a cortical neuron cell, a hippocampal neuron cell, a spinal cord motor neuron cell, or a murine cholinergic Neuro 2a cell.

In a further embodiment, the present invention provides a kit which comprises a construct of the present invention in a suitable container.

Contemplated methods of improving sensitivity of energy transfer between a donor label and an acceptor label include: (a) providing a construct comprises a donor label and acceptor label physically coupled through a linker, (a) including in the linker a cleavage site sequence; and (b) including a spacer in the linker between at least one of the donor and the cleavage site sequence and the acceptor and the cleavage site sequence, whereby the electronic coupling between the donor and the acceptor is increased. The constructs contemplated herein can be applied to whole cells, lysates, or any material that includes active peptidases.

While not wishing to be held to any particular theory or mechanism of action, it is contemplated that the spacer improves sensitivity and specificity by increasing the electronic coupling between the donor and the acceptor, which in turn is caused by (a) reducing the tertiary structure distance between the donor and the acceptor, and (b) providing an electronic hop between the donor and the acceptor.

In preferred embodiments, the construct is a protein-based construct, the linker is a peptide sequence, the cleavage site sequence comprises a SNARE protein, or a fragment or mutein thereof, and the spacer comprises at least 3, 5, 7, 10, 12, and 15 amino acids. The spacer can include a sequence selected from the group consisting of (GGGGS)n [Seq ID 7] and (EAAAK)n, [Seq ID 8] where n is 1-3.

Also disclosed herein is a method for detecting a *botulinum* neurotoxin, the method comprising (a) providing a construct described hereinabove, wherein the linker is substrate protein or a cleavable fragment thereof corresponding to the *botulinum* neurotoxin to be detected, (b) exposing the construct to a sample suspected of containing a *botulinum* neurotoxin under a condition under which the *botulinum* neurotoxin cleaves the protein substrate or a fragment thereof, and (c) detecting and comparing the FRET signal before and after the construct is exposed to the sample, wherein a decrease in FRET indicates the presence of *botulinum* neurotoxin in the sample. In a preferred embodiment, additional $Zn^{2+}$ is added to the sample to be detected. The method of the invention is suitable for the detection of a *botulinum* neurotoxin selected from the group consisting of BoNT/A, E, and C, and the corresponding substrate protein is SNAP-25 or a cleavable fragment thereof. The method of the present invention is also suitable for the detection of BoNT/B, D, F or G, using synaptobrevin (Syb) or a cleavable fragment thereof as a corresponding substrate protein. Similarly, the method of the present invention is suitable for detecting BoNT/C, with SNAP-25 or a cleavable fragment thereof as a corresponding substrate protein.

In a preferred embodiment, for the method of the present invention, FRET is detected by a method selected from the group consisting 1) measuring fluorescence emitted at the acceptor (A) emission wavelength and donor (D) emission wavelength, and determining energy transfer by the ratio of the respective emission amplitudes; 2) measuring fluorescence lifetime of D; 3) measuring photobleaching rate of D; 4) measuring anisotropy of D or A; and 5) measuring the Stokes shift monomer/excimer fluorescence.

The present invention also provides a method for screening for an inhibitor of a *botulinum* neurotoxin, comprising providing a cell genetically engineered to express a construct as described above, wherein the linker in the construct is a substrate peptide corresponding to the *botulinum* toxin; exposing said cell to the *botulinum* neurotoxin in the presence of a candidate inhibitor compound; and detecting FRET signals of the cell before and after said exposing to the *botulinum* toxin, wherein an observation of substantially no decrease in FRET, compared to a cell exposed to the *botulinum* neurotoxin in the absence of the candidate inhibitor, indicates that the candidate inhibitor is capable of inhibiting the *botulinum* neurotoxin. Preferably, the candidate compound is among a library of compounds and the method is a high throughput method.

In a further embodiment, the present invention provides a method for detecting a *botulinum* neurotoxin, the method comprising depositing a layer of a BoNT target peptide onto a metal surface, exposing said metal surface having BoNT target peptide on its surface to a sample suspected of containing a corresponding BoNT, under conditions to allow the BoNT to cleave the target peptide on the metal surface, and measuring any decrease in the molecular weight of the target peptide bound to the metal surface as a result of BoNT cleavage via surface plasmon resonant imaging.

Another embodiment of the present inventions is a method for detecting a *botulinum* neurotoxin, the method comprising, a) providing a construct described herein, wherein the linker is a substrate protein or a cleavable fragment thereof corresponding to the *botulinum* neurotoxin to be detected, and wherein the construct is anchored to a plasma membrane of a cell, such that the linker protein adopts a conformation with which FRET occurs between the donor and acceptor fluorophore, b) exposing the construct to a sample suspected of containing a *botulinum* neurotoxin under a condition under which the *botulinum* neurotoxin cleaves the protein substrate or a fragment thereof, and c) detecting and comparing the FRET signal before and after the construct is exposed to the sample, wherein a decrease in FRET indicates the presence of *botulinum* neurotoxin in the sample.

The present invention further provides a molecular construct comprising a linker peptide, a first fluorophore moiety and a second fluorophore moiety, wherein the linker peptide is a substrate of a *botulinum* neurotoxin selected from the group consisting of synaptobrevin, syntaxin and SNAP-25, or a fragment thereof that is able to be cleaved by the *botulinum* neurotoxin, and wherein emission spectrum of the first fluorophore moiety is detectably different from the excitation spectrum of the second fluorophore moiety. Preferably, the linker is a full-length protein of the substrate synaptobrevin, syntaxin or SNAP-25. Preferably, the construct is anchored to a vesicle, which may or may not be inside a cell. The present further provides a polynucleotide construct encoding the above polypeptide construct.

The present invention further provides a method for detecting a *botulinum* neurotoxin, the method comprising a) providing a peptide construct as described above, b) exposing the construct to a sample suspected of containing a *botulinum* neurotoxin under a condition under which the *botulinum* neurotoxin cleaves the protein substrate or a fragment thereof, and c) detecting spatial separation of the fluorescence signals of the first and second fluorophores, wherein occurrence of spatial separation indicates the presence of *botulinum* neurotoxin in the sample. Preferably, the vesicle is inside a live cell, the linker peptide is CFP-SNAP-25 (1-197) linked to SNAP-25 (198-206)-YFP, wherein detection of CFP fluorescence but not YFP fluorescence indicates the existence of presence of *botulinum* neurotoxin in the sample.

Various objects, features, aspects and advantages of the inventive subject matter will become more apparent from the following detailed description of preferred embodiments, along with the accompanying drawings in which like numerals represent like components.

BRIEF DESCRIPTION OF THE DRAWING

FIG. 1A is a design of the bio-sensor constructs. CFP and YFP are connected via a fragment of synaptobrevin (amino acid 33-94, upper panel), or SNAP-25 (amino acid 141-206, lower panel), respectively. The cleavage sites for each *botulinum* neurotoxin on these fragments are labeled. FIG. 1B shows that CFP and YFP function as a donor-acceptor pair for FRET, in which the excitation of CFP results in YFP fluorescence emission (upper panel). Energy transfer between linked CFP and YFP is abolished after cleavage of the synaptobrevin or SNAP-25 fragment with *botulinum* neurotoxins (lower panel). The optimal excitation wavelength for CFP is 434 nM, and the emission peak is 470 nM for CFP, and 527 nM for YFP.

FIG. 2A shows the emission spectra of the recombinant his$_6$-tagged CFP and YFP alone (300 nM), as well as the mixture of these two proteins (1:1). The fluorescence signals were collected from 450 to 550 nM using a PTIQM-1 fluorometer in Hepes buffer (50 mM Hepes, 2 mM DTT, and 10 $\mu$M ZnCl$_2$, pH 7.1). The excitation wavelength is 434 nM, the optimal for CFP. The YFP protein only elicits a small fluorescence emission signal by direct excitation at 434 nM. FIG. 2B shows the emission spectra of recombinant his$_6$-tagged CFP-SybII-YFP, colleted as described in panel FIG. 2A. The arrow indicates the YFP emission peak resulted from FRET. FIG. 2C shows the emission spectra of recombinant his$_6$-tagged CFP-Snap-25-YFP as described in panel FIG. 2C.

FIG. 5 shows the sensitivity of the bio-sensor assay using a plate-reader. A): 300 nM CFP-SNAP-25-YFP were mixed with various concentration of BoNT/A or E in a 96-well plate, the total volume is 100 $\mu$l per well. The plate was incubated at 37 $^\circ$C for 4 hours and then scanned with a plate-reader (upper panel). The FRET ratio was plotted against the log value of the toxin concentration. The $EC_{50}$ values for each curve are listed in the table on the lower panel. Each data point represents the mean of three independent experiments. B): 300 nM CFP-SybII-YFP were mixed with various concentration of BoNT/B or F. The data were collected and plotted as described in panel A.

FIG. 6 depicts the monitoring of *botulinum* neurotoxin activity in living cells. A): CFP-SNAP-25-YFP was expressed in wild type PC12 cells. The entry and catalytic activity of BoNT/A (50 nM) was monitored by recording the FRET ratio change that results from CFP-SNAP-25-YFP cleavage inside the cells. The FRET ratio was averaged from a total of 53 toxin treated cells and 53 control cells. Treatment with BoNT/A for 72 hours reduced the FRET ratio of the entire population of cells by a significant degree (P<1.47E-5). B): PC12 cells that express syt II were transfected with CFP-SybII-YFP and treated with BoNT/B (30 nM). The entry and catalytic activity of BoNT/B were monitored by recording the FRET ratio change as in panel (A); 73 toxin treated and 73 control cells were analyzed. Treatment with BoNT/B for 72 hours reduced the FRET ratio of the entire population of cells by a significant degree (P<2E-10).

FIG. 7 shows the monitoring BoNT/A activity in living cells using according to the present invention. (a). Measuring the FRET signal of toxin sensors in living cells. CFP-SNAP-25(141-206)-YFP was used to transfect PC12 cells. This sensor appeared to be soluble in cells. Three images using different filter set (CFP, FRET and YFP) were taken for each cell sequentially, using exactly the same settings. Images were color coded to reflect the fluorescence intensity in arbitrary units as indicated in the look-up table on the left. The corrected FRET value was calculated by subtracting the crosstalk from both CFP and YFP from the signals collected using the FRET filter set, as detailed in the Methods. (b). PC12 cells transfected with CFP-SNAP-25(141-206)-YFP were used to detect BoNT/A activity. Fifty nM BoNT/A holotoxin was added to the culture medium and 80 cells were analyzed after 96 hours. The corrected FRET signal was normalized to the CFP fluorescence signal and plotted as a histogram with the indicated bins. Control cells were transfected with the same sensor but were not treated with toxins, and they were analyzed in parallel. Incubation with BoNT/A shifted the FRET ratio (corrected FRET/CFP) among the cell population, indicating the sensor proteins were cleaved by BoNT/A in cells. However, the shift was small, indicating that the cleavage was not efficient in cells. (c). Left panel: an efficient toxin sensor was built by linking CFP and YFP through full-length SNAP-25 (amino acid 1-206), and tested for detecting BoNT/A activity in cells. This CFP-SNAP-25(FL)-YFP fusion protein was localized primarily to plasma membranes in cells via palmitoylation at its four cysteines (left panel, upper frames of the middle panel). Middle panel: PC 12 cells were transfected with the CFP-SNAP-25(FL)-YFP sensor and used to detect BoNT/A activity. Fifty nM BoNT/A holotoxin was added to the culture medium and the FRET signals of 200 cells were analyzed after 48 and 96 hours as described in panel (a). Control cells were transfected with toxin sensors but were not treated with toxins, and they were analyzed in parallel. The images of representative cells were shown in the middle panel. This sensor yielded significant FRET (upper "corrected FRET" frame of the middle panel). The FRET signal was abolished after cells were treated with BoNT/A (96 h, lower "corrected FRET" frame of the middle panel). Note: one of the cleavage products, the C-terminus of SNAP-25 tagged with YFP, was degraded after toxin cleavage. Thus, the fluorescence signal of YFP was significantly decreased in toxin-treated cells (lower "YFP" frame). Right panel: the FRET ratios are plotted as a histogram with indicated bins as described in panel (b). (d). PC12 cells were transfected with CFP-SNAP-25(Cys-Ala)-YFP (full length SNAP-25 with Cys 85,88,90,92 Ala mutations, left panel). This protein has diffusely distributed throughout the cytosol, and lacked the strong FRET signal observed for CFP-SNAP-25(FL)-YFP (right panel, "corrected FRET" frame). (e). PC12 cells were transfected with CFP-SNAP-25(FL)-YFP and CFP-SNAP-25(Cys-Ala)-YFP. Cells were then treated with (+, intact cells) or without (−, intact cells) BoNT/A (50 nM, 72 h), and were harvested. Half of the cell extracts from samples that are not been exposed to BoNT/A were also incubated with (+, in vitro) or without (−, in vitro) reduced BoNT/A in vitro (200 nM, 30 min, 37.degree. C.), served as controls to show the cleavage products (two cleavage products are indicated by arrows). The same amount of each sample (30.mu.g cell lysate) was loaded to one SDS-page gel and subjected to immunoblot analysis using an anti-GFP antibody. While CFP-SNAP-25(FL)-YFP underwent significant cleavage in intact cells, there was no detectable cleavage of CFP-SNAP-25(Cys-Ala)-YFP in cells, indicating the membrane anchoring is important for efficient cleavage by BoNT/A in living cells. Note: only one cleavage product (CFP-SNAP-25(1-197)) was detected in toxin treated cells, indicating that the other cleavage product (SNAP-25(198-206)-YFP) was largely degraded in cells.

FIG. 13 is a block diagram illustrating the steps of a method for detecting *botulinum* neurotoxin using the construct of the present invention.

DETAILED DESCRIPTION

Figure 1:
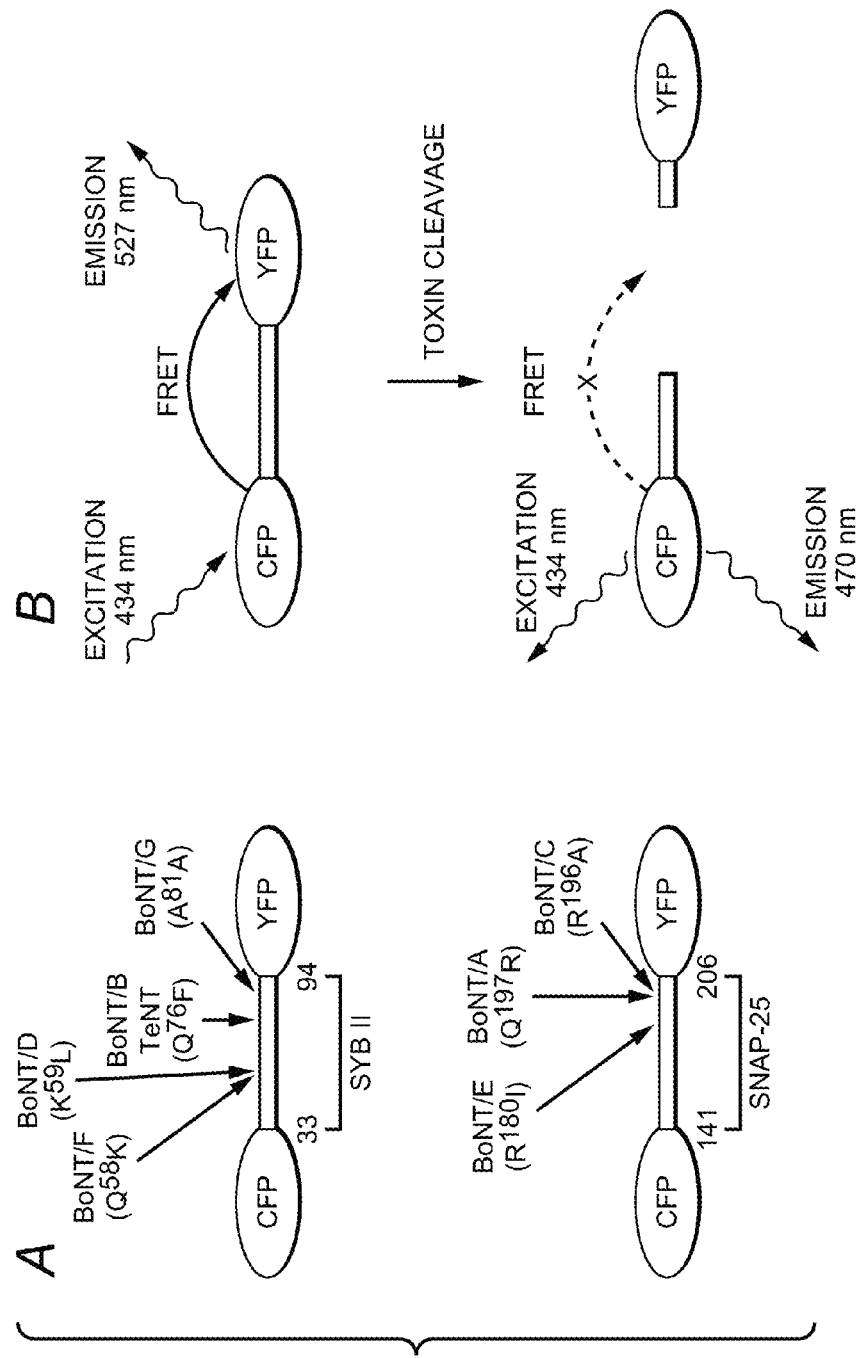
FIG. 1 is a schematic depiction of the CFP-YFP based bio-sensors for monitoring *botulinum* neurotoxin protease activity.

The present invention provides novel compositions and methods based on fluorescence resonance energy transfer (FRET) between fluorophores linked by a peptide linker which is a substrate of a BoNT and can be cleaved by the toxin, to detect *botulinum* neurotoxins and monitor their substrate cleavage activity, preferably in real time. The method and compositions of the present invention allow for the detection of pico-molar level BoNTs within hours, and can trace toxin enzymatic kinetics in real time. The methods and compositions can further be used in high-throughput assay systems for large-scale screening of toxin inhibitors, including inhibitors of toxin cellular entry and translocation through vesicle membrane using cultured cells. The present invention is also suitable for monitoring *botulinum* neurotoxin activity in living cells and neurons.

In another embodiment, the present invention provides a construct and method of using the construct which comprises full-length SNAP-25 and Syb proteins as the linkers, as fluorescent biosensors that can detect toxin activity within living cells. Cleavage of SNAP-25 abolished CFP/YFP FRET signals and cleavage of Syb resulted in spatial redistribution of the YFP fluorescence in cells. The present invention provides a means to carry out cell based screening of toxin inhibitors and for characterizing toxin activity inside cells. The present invention also discloses that the sub-cellular localization of SNAP-25 and Syb affects efficient cleavage by BoNT/A and B in cells, respectively.

Fluorescent Resonance Energy Transfer (FRET) is a tool which allows the assessment of the distance between one molecule and another (e.g. a protein or nucleic acid) or between two positions on the same molecule. FRET is now widely known in the art (for a review, see Matyus, (1992) J. Photochem. Photobiol. B: Biol., 12:323). FRET is a radiationless process in which energy is transferred from an excited donor molecule to an acceptor molecule. Radiationless energy transfer is the quantum-mechanical process by which the energy of the excited state of one fluorophore is transferred without actual photon emission to a second fluorophore. The quantum physical principles are reviewed in Jovin and Jovin, 1989, Cell Structure and Function by Microspectrofluorometry, eds. E. Kohen and J. G. Hirschberg, Academic Press. Briefly, a fluorophore absorbs light energy at a characteristic wavelength. This wavelength is also known as the excitation wavelength. The energy absorbed by a fluorochrome is subsequently released through various pathways, one being emission of photons to produce fluorescence. The wavelength of light being emitted is known as the emission wavelength and is an inherent characteristic of a particular fluorophore. In FRET, that energy is released at the emission wavelength of the second fluorophore. The first fluorophore is generally termed the donor (D) and has an excited state of higher energy than that of the second fluorophore, termed the acceptor (A).

An essential feature of the process is that the emission spectrum of the donor overlap with the excitation spectrum of the acceptor, and that the donor and acceptor be sufficiently close.

In addition, the distance between D and A must be sufficiently small to allow the radiationless transfer of energy between the fluorophores. Because the rate of energy transfer is inversely proportional to the sixth power of the distance between the donor and acceptor, the energy transfer efficiency is extremely sensitive to distance changes. Energy transfer is said to occur with detectable efficiency in the 1-10 nm distance range, but is typically 4-6 nm for optimal results. The distance range over which radiationless energy transfer is effective depends on many other factors as well, including the fluorescence quantum efficiency of the donor, the extinction coefficient of the acceptor, the degree of overlap of their respective spectra, the refractive index of the medium, and the relative orientation of the transition moments of the two fluorophores.

The present invention provides a construct ("FRET construct") which comprises a fluorophore FRET donor and an acceptor linked by linker peptide ("substrate peptide") that is cleavable by a corresponding BoNT. In the presence of a BoNT, the linker peptide is cleaved, thereby leading to a decrease in energy transfer and increased emission of light by the donor fluorophore. In this way, the proteolysis activity of the toxin can be monitored and quantitated in real-time.

As used herein with respect to donor and corresponding acceptor fluorescent moieties, "corresponding" refers to an acceptor fluorescent moiety having an emission spectrum that overlaps the excitation spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radioactive energy transfer can be produced.

As used herein with respect to substrate peptide and BoNT, "corresponding" refers to a BoNT toxin that is capable of acting on the linker peptide and cleaves at a specific cleavage site.

Fluorescent donor and corresponding acceptor moieties are generally chosen for (a) high efficiency Forster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, Helium-Cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

A skilled artisan will recognize that many fluorophore molecules are suitable for FRET. In a preferred embodiment, fluorescent proteins are used as fluorophores. Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2-,2'-disulfonic acid derivatives. Representative acceptor fluorescent moieties, depending upon the donor fluorescent moiety used, include LC-Red 640, LC-Red 705, Cy5, Cy5.5, Lissamine rhodamine B sulfonyl chloride, tetramethyl rhodamine isothiocyanate, rhodaminexisothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

Table 1 lists other examples of chemical fluorophores suitable for use in the invention, along with their excitation and emission wavelengths.

Certain naturally occurring amino acids, such as tryptophan, are fluorescent. Amino acids may also be derivatized, e.g. by linking a fluorescent group onto an amino acid (such as linking AEDANS to a Cys), to create a fluorophore pair for FRET. The AEDANS-Cys pair is commonly used to detect protein conformational change and interactions. Some other forms fluorescence groups have also been used to modify amino acids and to generate FRET within the protein fragments (e.g. 2,4-dinitrophenyl-lysine with S—(N-[4-methyl-7-dimethylamino-coumarin-3-yl]-carboxamidomethyl)-cysteine-).

In another embodiment, which is especially suitable for using in live cells, green fluorescent protein (GFP) and its various mutants are used as the fluorophores. Examples of fluorescent proteins which vary among themselves in excitation and emission maxima are listed in Table 1 of WO 97/28261 (Tsien et al., 1997), which is incorporated herein by reference. These (each followed by [excitation max./emission max.] wavelengths expressed in nanometers) include wild-type Green Fluorescent Protein [395(475)/508] and the cloned mutant of Green Fluorescent Protein variants P4 [383/447], P4-3 [381/445], W7 [433(453)/475(501)], W2 [432(453)/408], S65T [489/511], P4-1 [504(396)/480], S65A [471/504], S65C [479/507], S65L [484/510], Y66F [360/442], Y66W [458/480], IOC [513/527], WIB [432(453)/476(503)], Emerald [487/508] and Sapphire [395/511]. Red fluorescent proteins such as DsRed (Clontech) having an excitation maximum of 558 nm and an emission maximum of 583 can also be used. This list is not exhaustive of fluorescent proteins known in the art; additional examples are found in the Genbank and SwissPro public databases.

TABLE 1

| Fluorophore | Excitation (nm) | Emission (nm) | Color |
|---|---|---|---|
| PKH2 | 490 | 504 | green |
| PKH67 | 490 | 502 | green |
| Fluorescein (FITC) | 495 | 525 | green |
| Hoechst 33258 | 360 | 470 | blue |
| R-Phycoerythrin (PE) | 488 | 578 | orange-red |
| Rhodamine (TRITC) | 552 | 570 | red |
| Quantum Red ™ | 488 | 670 | red |
| PKH26 | 551 | 567 | red |
| Texas Red | 596 | 620 | red |
| Cy3 | 552 | 570 | red |

GFP is a 27-30 KD protein, and can be fused with another protein, e.g. the target protein, and the fusion protein can be engineered to be expressed in a host cell, such as those of *E. coli*. GFP and its various mutants are capable of generating fluorescence in live cells and tissues. The mutation forms of GFP has slight amino acid differences within their fluorescence region which result in shifted spectrum. More mutations of GFP are expected to be created in the future to have distinct spectra. Among these GFP variants, BFP-YFP, BFP-CFP, CFP-YFP, GFP-DsRed, are commonly used as FRET donor-acceptor pairs to detect protein-protein interactions. These pairs are also suitable to detect protease cleavage of the linker region that links the pair.

The use of fluorescent proteins is preferred because they enable the use of a linker fragment of about 60 amino acids residues. Longer fragments usually are more sensitive to toxin recognition and cleavage, thus, results in a higher sensitivity for detecting toxin. As shown in the examples below, the EC50 for BoNT/A and E after 4 hour incubation with CFP-SNAP-YFP are as low as 15-20 pM (1-2 ng/ml), when measured with a widely used microplate spectrofluorometer (Spectra Max Gemini, Molecular Device). EC50 for BoNT/B and F are about 200-250 pM, and the sensitivity can be enhanced by increasing incubation time.

According to one embodiment of the present invention, two fluorophores are linked together by a linker of suitable length, such that FRET occurs. The linker is a fragment of a BoNT substrate protein. When exposed to a BoNT capable of cleaving the linker fragment, the two fluorophores are separated and FRET is abolished. The present invention provides accordingly a method for detecting BoNT by detecting the change in FRET. SNARE proteins from many species are suitable as substrate proteins for BoNT toxins, because these proteins are known to be conserved at the amino acid level. Many of these BoNT substrate proteins are known and available to be used or modified for use as a suitable linker peptide for the present invention. Some of the substrate proteins and their GenBank accession numbers are listed in

TABLE 1

| Protein | Origin | Accession # |
|---|---|---|
| syb 1 | mouse | NP-033522 |
| svb la | human | NP_055046 |
| syb 1 | rat | AAN85832 |
| syb | African frog | AAB88137 |
| syb | electric ray | A32146 |
| syb | California sea hare | P35589 |
| syb | Takifugu rubripes | AAB94047 |
| syb | drosophila | AAB28707 |
| syb II | mouse | NP_033523 |
| syb II | African frog | P47193 |
| Syb II | rabbit | AAN14408 |
| syb II | rat | NP-036795 |
| syb II | human | AAH19608 |
| syb 3 | human | AAP36821 |
| SNAP25-1 | Zebra fish | AAC64289 |
| SNAP25-A | human | NP-003072 |
| SNAP25a | American frog | AAO13788 |
| SNAP25 | mouse | XP_130450 |
| SNAP25 | rat | NP_112253 |
| SNAP25 | goldfish | 150480 |
| SNAP25-b | Zebra fish | NP_571509 |
| SNAP25b | American frog | AAO13789 |
| SNAP25-3 | human | CAC34535 |

Each BoNT toxin is known to cleave a specific peptide bond between two specific amino acids within the toxin cleavage site. Table 3 below lists the amino acid pairs for each BoNT toxin. These pairs of amino acid sequence, however, are not sufficient for toxin recognition and cleavage. For example, BoNT/A cleaves SNAP-25 at Q(197)-R(198) of the rat SNAP-25 sequence (GenBank accession No: NP.sub.—112253), but not Q(15)-R(16). Generally, there is no conserved amino acid sequence as the recognition site; rather, the toxins are believed to recognize the tertiary, rather than the primary, structure of their target protein. Nevertheless, a very short fragment of the substrate protein is sufficient for toxin recognition and cleavage, regardless of its species origin, as long as they have the two amino acid residues at the toxin cleavage site listed above in Table 3 below.

The linker protein or peptide can be as long as the full-length of the BoNT substrate protein. Preferably the linker is a shorter fragment of the substrate protein. A full-length substrate linker may be too long for efficient FRET, and a shorter fragment is more effective and easier to produce than the full-length protein. On the other hand, as indicated above, the linker peptide should be above certain minimum length, because below such a minimum length, cleavage of the linker peptide by the respective BoNTs becomes inefficient.

TABLE 3

Peptide Bonds Recognized and Cleaved by BoNT Toxins

| Toxin | Cleavage Site | Putative Minimum Recognition Sequence |
|---|---|---|
| BoNT/A | Q-R | Glu-Ala-Asn-Gln-Arg-Ala-Thr-Lys (SEQ ID NO: 1) |
| BoNT/B | Q-F | Gly-Ala-Ser-Gln-Phe-Glu-Thr-Ser (SEQ ID NO: 2) |
| BoNT/C (SNAP25) | R-A | Ala-Asn-Gln-Arg-Ala-Thr-Lys-Met (SEQ ID NO: 3) |
| BoNT/C (Syntaxin) | K-A | Asp-Thr-Lys-Lys-Ala-Val-Lys-Phe (SEQ ID NO: 4) |
| BoNT/D | K-L | |
| BoNT/E | R-I | Gln-Ile-Asp-Arg-Ile-Met-Glu-Lys (SEQ ID NO: 5) |
| BoNT/F | Q-K | Glu-Arg-Asp-Gln-Lys-Leu-Ser-Glu (SEQ ID NO: 6) |
| BoNT/G | A-A | |

Using syb II and BoNT/B as an example, Table 4 below illustrates the relationship between linker-peptide length and toxin cleavage rate. The full-length rat syb II protein (GenBank No: NP.sub.—036795) has 116 amino acids, of which amino acid 1-94 at the amino terminus is the cytoplasmic domain and the rest is the transmembrane domain. As Table 1 makes clear, within certain limit, a shorter fragment is cleaved by the toxin at a slower rate (data from Foran et al., Biochemistry 33:15365, 1994).

As can be seen from Table 4, tetanus neurotoxin (TeNT) requires a longer fragment (33-94) for optimum cleavage than BoNT/B (55-94). A fragment consisting of 60-94 has been used in several studies including several peptide-based toxin assay methods (Schmidt et al., 2003, supra, and Schmidt et al., 2001, Analytical Biochemistry, 296: 130-137).

For BoNT/A, the 141-206 fragment of SNAP-25 is required for retaining most of the toxin sensitivity (Washbourne et al., 1997, FEBS Letters, 418:1). There are also other reports that a shorter peptide, amino acids 187-203 of SNAP25, is sufficient to be cleaved by BoNT/A (, 2001). The minimum site for BoNT/A is: Glu-Ala-Asn-Gln-Arg-Ala-Thr-Lys (SEQ ID NO: 1). BoNT/A cleave Gln-Arg.

TABLE 4

Relationship Between Syb II fragment Length and Cleavage Rate

| Syb II Fragment Length | Relative cleavage rate by BoNT/B | % Relative cleavage rate by TeNT |
|---|---|---|
| full length 1-116 | 100 (%) | 100 (%) |
| 33-94 | 100 | 100 |
| 45-94 | 121 | 1.1 |
| 55-94 | 105 | 0.4 |
| 65-94 | 7 | 0.3 |

Using full-length SNAP-25 as the linker sequence between CFP and YFP inside PC12 cells, preliminary results indicate that FRET signals obtained are stronger than those obtained using a shorter fragment, enough to be detected using a conventional lab microscope. It is believed that in PC12 cells the rate of cleavage of full-length SNAP-25 by BoNT/A is faster and more consistent from cell to cell than the short fragment, likely due to the fact that full-length SNAP-25 is targeted onto plasma membrane, on to which the BoNT/A light chain may also be targeted and anchored.

For BoNT/B, a fragment as short as between residues 60-94 was found to be as effective as a fragment between residues 33-94. Preferably, a fragment between 33-94 is used for BoNT/B and TeNT. Both toxins cleave between Gln and Phe, and the minimum sequence for cleavage is believed to be: Gly-Ala-Ser-Gln-Phe-Glu-Thr-Ser (SEQ ID NO: 2). There are indications that BoNT/B light chain may be targeted and anchored on synaptic vesicles, it may be desirable to also target, via signal sequences, a FRET construct of the present invention onto synaptic vesicles to achieve increased cleavage efficient inside cells.

BoNT/C cleaves both SNAP25 and Syntaxin, and is believed to cleave at a very slow rate if the substrate is in solution. Native SNAP25 and Syntaxin that reside on the cell membrane are cleaved most efficiently by BoNT/C. The minimum cleavage sequence for SNAP25 is: Ala-Asn-Gln-Arg-Ala-Thr-Lys-Met (SEQ ID NO: 3), where cleavage occurs between Arg-Ala; for Syntaxin, the minimum cleavage sequence is Asp-Thr-Lys-Lys-Ala-Val-Lys-Phe (SEQ ID NO: 4), and cleavage occurs at Lys-Ala.

BoNT/E requires a minimum sequence of: Gln-Ile-Asp-Arg-Ile-Met-Glu-Lys (SEQ ID NO: 5), and cleaves between Arg-Ile.

BoNT/F cleaves Gln-Lys. Schmidt et al. (Analytical Biochemistry, 296: 130-137 (2001)) reported that a 37-75 fragment of syb II retains most of toxin sensitivity, and the minimum sequence is: Glu-Arg-Asp-Gln-Lys-Leu-Ser-Glu (SEQ ID NO: 6).

From the above discussion on the minimum cleavage sites and the relationship between FRET signal strength and linker length, and between cleavage efficiency and linker length, a person skilled in the art can easily choose suitable linker length to achieve optimal balance between FRET signal strength and cleavage efficiency.

Preferably, the linker length is anywhere between about 8 a.a. to about 100 a.a., preferably between 10-90, more preferable between 20-80, between 30-70, between 40-60 a.a. long, depending on the specific substrate and toxin combination.

In one embodiment, a linker protein or fragments thereof may be first purified, or peptides were first synthesized, and then the fluorescence groups were added onto certain amino acids through chemical reaction. A fluorescent label is either attached to the linker polypeptide or, alternatively, a fluorescent protein is fused in-frame with a linker polypeptide, as described below. The above discussion makes clear that while short substrate fragments are desirable for toxin detection specificity, longer fragments may be desirable for improved signal strength or cleavage efficiency. It is readily recognized that when the substrate protein contains more than one recognition site for one BoNT, a position result alone will not be sufficient to identify which specific toxin is present in the sample. In one embodiment of the present invention, if a longer substrate fragment, especially a full-length substrate protein, is used, the substrate may be engineered, e.g. via site-directed mutagenesis or other molecular engineering methods well-known to those skilled in the art, such that it contains only one toxin/protease recognition site. See e.g. Zhang et al, 2002, Neuron 34:599-611 "Ca2+-dependent synaptotagmin binding to SNAP-25 is essential for Ca2+ triggered exocytosis" (showing that SNAP-25 having mutations at BoNT/E cleavage site (Asp 179 to Lys) is resistant to BoNT/E cleavage, but behaves normally when tested for SNARE complex formation). In a preferred embodiment, the method of the present invention uses a combination of specificity engineering and length optimization to achieve optimal signal strength, cleavage efficiency and toxin/serotype specificity.

In a preferred embodiment, the fluorophores are suitable fluorescent proteins linked by a suitable substrate peptide. A FRET construct may then be produced via the expression of recombinant nucleic acid molecules comprising an in-frame fusion of sequences encoding such a polypeptide and a fluorescent protein label either in vitro (e.g., using a cell-free transcription/translation system, or instead using cultured cells transformed or transfected using methods well known in the art). Suitable cells for producing the FRET construct may be a bacterial, fungal, plant, or an animal cell. The FRET construct may also be produced in vivo, for example in a transgenic plant, or in a transgenic animal including, but not limited to, insects, amphibians, and mammals. A recombinant nucleic acid molecule of use in the invention may be constructed and expressed by molecular methods well known in the art, and may additionally comprise sequences including, but not limited to, those which encode a tag (e.g., a histidine tag) to enable easy purification, a linker, a secretion signal, a nuclear localization signal or other primary sequence signal capable of targeting the construct to a particular cellular location, if it is so desired.

As low as 300 nM proteins is enough to generate sufficient fluorescence signals that can be detected using a microplate spectrofluorometer. The fluorescence signal change can be traced in real time to reflect the toxin protease enzymatic activity. Real time monitoring measures signal changes as a reaction progresses, and allows both rapid data collection and yields information regarding reaction kinetics under various conditions. FRET ratio changes and degrees of cleavage may be correlated, for example for a certain spectrofluorometer using a method such as HPLC assay in order to correlate the unit of kinetic constant from the FRET ratio to substrate concentration.

Figure 10:
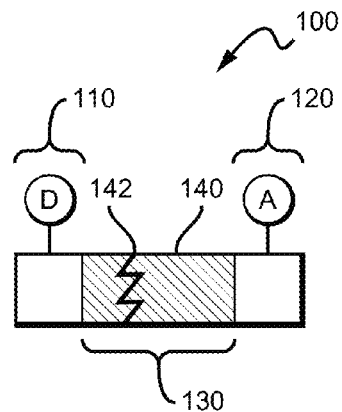
FIG. 10 is a schematic depicting a prior art construct, having a linker that includes a cleavage site sequence disposed between a donor label and an acceptor label.

FIG. 10, is a schematic of a prior art construct 100, having a linker 130 that includes a cleavage site sequence 140 and cleavage site 142 disposed between a donor label 110 and an acceptor label 120. This type of prior art construct works reasonably well for detecting BoNTs. However, exemplary construct 100a of FIG. 11a, surprisingly, has an enhanced sensitivity for detecting BoNTs due the inclusion of spacer 150a within linker 130a.

Figure 11A:
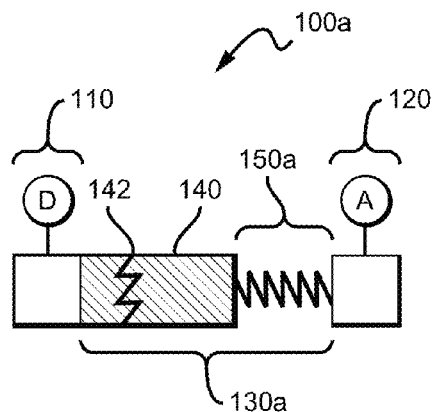
FIG. 11a is a schematic depicting one embodiment of the construct of the present invention, having a linker that includes a cleavage site sequence and a spacer, the spacer being disposed between the cleavage site sequence and the acceptor label.

FIG. 11a is a schematic depicting one embodiment of the construct 100a of the present invention, having a linker 130a that includes a cleavage site sequence 140, a cleavage site 142, and a spacer 150a. Spacer 150a is disposed between the cleavage site sequence 140 and the acceptor label 120. Preferably, construct 100a is selected from the group consisting of CFP-(SGLRSRA)-SNAP-25-(SNS)-YFP, and CFP-(SGLRSRA)-synaptobrevin-(SNS)-YFP.

Donor label 110 and acceptor label 120 are positioned to provide an electronic coupling such that the donor label can transfer energy to the acceptor label by a dipole-dipole coupling mechanism, including but not limited to Förster resonance energy transfer (FRET).

Linker peptide 130a is a substrate of a *botulinum* neurotoxin selected from the group consisting of synaptobrevin (VAMP), syntaxin and SNAP-25, or a fragment thereof that can be recognized and cleaved by the *botulinum* neurotoxin. These proteins collectively are referred to as the SNARE proteins. Linker 130a can have a primary structure length of any suitable length, including for example, greater than or equal to 5 nm, 8 nm, 10 nm, 12 nm, 14 nm, and 20 nm.

Spacer 150a can have any suitable number of amino acids, but preferably at least 3, 5, 7, 10, 12, or 15 amino acids. Spacer 150a can include a sequence selected from the group consisting of (GGGGS)n and (EAAAK)n, where n is 1-3. Alternatively, spacer 150a can comprise a SNARE protein, motif, or mutein. Although spacer 150a increases the primary structure distance between donor label 110 and acceptor label 120, spacer 150a advantageously increases the electronic coupling (FRET effect) between donor label 110 and acceptor label 120 relative to a corresponding construct without the spacer. The enhanced electronic coupling occurs because spacer 150a reduces the tertiary structure distance between donor label 110 and acceptor label 120, thus allowing increase electronic coupling.

Cleavage site sequence 140 can comprise (a) a SNARE protein, motif, mutein, and (b) a spacer with at least 5 amino acids, wherein the spacer includes a sequence selected from the group consisting of (GGGGS)n and (EAAAK)n, where n is 1-3.

Figure 11B:
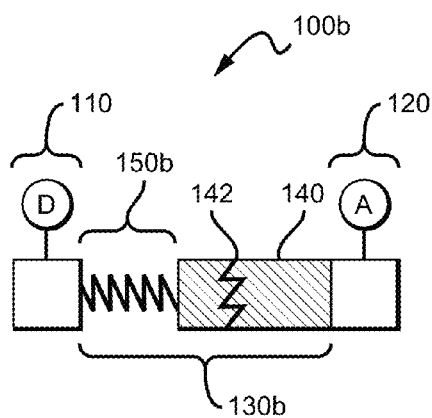
FIG. 11b is a schematic depicting an alternative embodiment of the construct of the present invention, having a linker that includes a cleavage site sequence and a spacer, the spacer being disposed between the donor label and the cleavage site sequence.

Construct 100b of FIG. 11b is similar to construct 100a of FIG. 11a except that linker 130b has spacer 150b disposed between the donor label 110 and the cleavage site sequence 140.

Figure 11C:
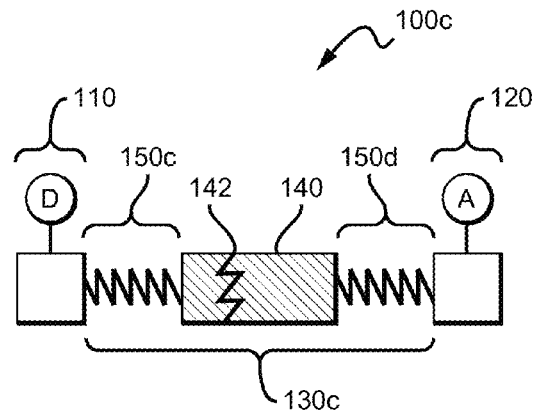
FIG. 11c is a schematic depicting another alternative embodiment of the construct of the present invention, having a linker that includes a cleavage site sequence and a spacer, the spacer being disposed between the donor and the cleavage site sequence and cleavage site sequence and the acceptor label.

Construct 100c of FIG. 11c is similar to construct 100a of FIG. 11a except that linker 130b has (a) spacer 150c disposed between donor label 110 and cleavage site sequence 140 and (b) spacer 150d disposed between cleavage site sequence 140 and acceptor label 120.

Figure 12:
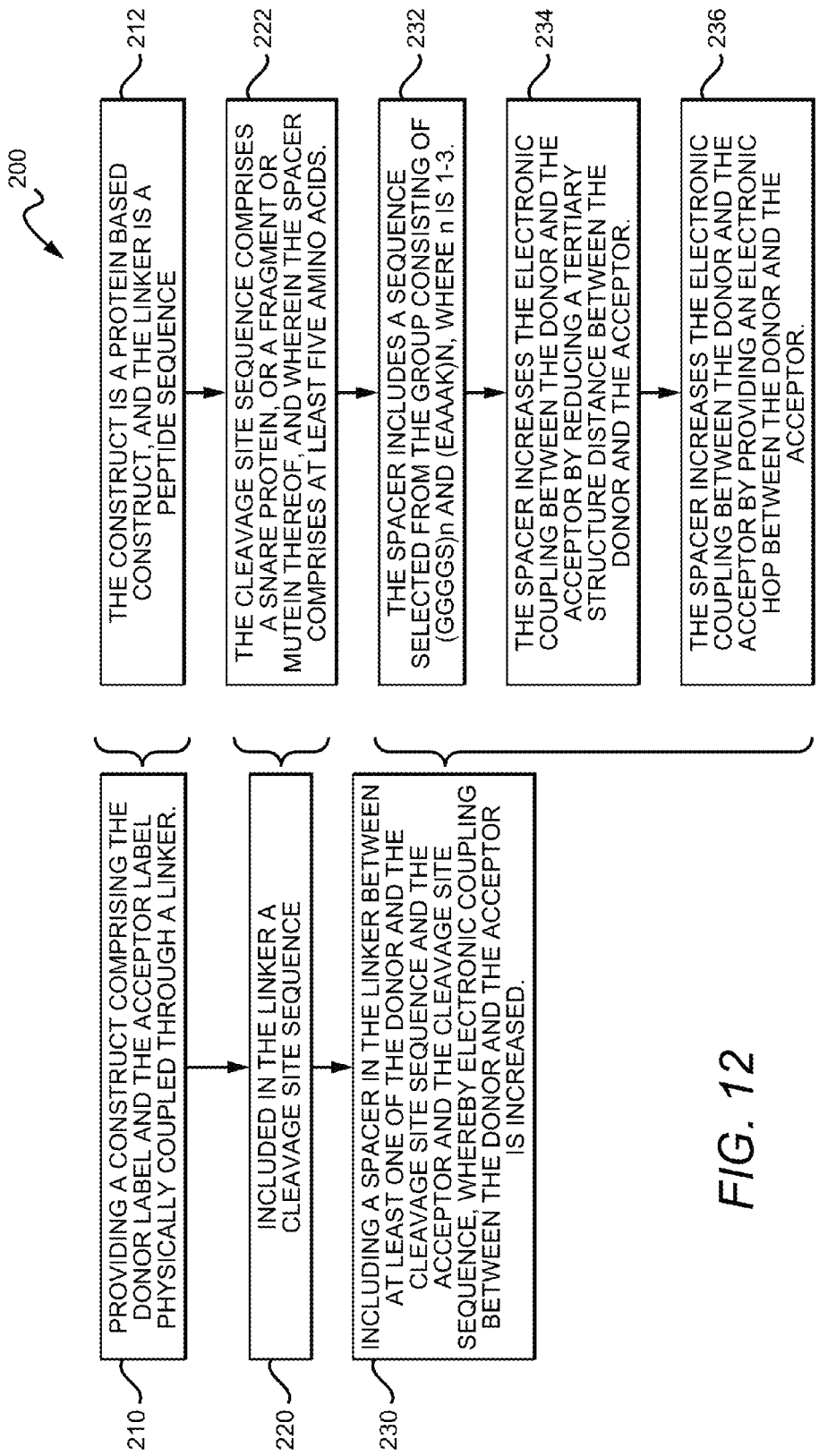
FIG. 12 is a block diagram illustrating the steps of a method of improving sensitivity of energy transfer between a donor label and an acceptor label using the construct of the present invention.

FIG. 12 illustrates the steps of a method 200 for improving the sensitivity of energy transfer between the donor label and the acceptor label using the construct of FIGS. 11a-11c. Step 210 is comprised of providing a construct according to FIGS. 11a-11c comprising the donor label and the acceptor label being physically coupled through a linker. The construct is a protein based construct, and the linker is a peptide sequence 212. Step 220 is comprised of including in the linker a cleavage site sequence. Optionally the cleavage site sequence comprises a SNARE protein, or a fragment or mutein thereof, and the spacer comprises at least five amino acids 222. Step 230 is comprised of including a spacer in the linker between at least one of the donor and the cleavage site sequence and the acceptor and the cleavage site sequence, whereby electronic coupling between the donor and the acceptor is increased by (a) reducing a tertiary structure distance between the donor and the acceptor 234, and (b) providing an electronic hop between the donor and the acceptor 236. Optionally, the spacer includes a sequence selected from the group consisting of (GGGGS)n and (EAAAK)n, where n is 1-3 232.

FIG. 13 illustrates the steps of a method 300 for detecting botulinum neurotoxin using the construct of FIGS. 11a-11c. Step 310 is comprised of providing a construct of claim 1, wherein a linker is a substrate protein or a cleavable fragment thereof of the botulinum neurotoxin to be detected. Step 320 is comprised of exposing the construct to a sample suspected of containing the botulinum neurotoxin under a condition under which the botulinum neurotoxin cleaves the substrate protein or the fragment thereof. And step 330 is comprised of detecting and comparing a FRET signal before and after the construct is exposed to the sample, wherein a decrease in FRET indicates the presence of botulinum neurotoxin in the sample.

The method of the present invention is highly sensitive, and as a consequence, can be used to detect trace amount of BoNTs in environmental samples directly, including protoxins inside Botulinum bacterial cells. Accordingly, the present invention further provides a method for toxin detection and identification directly using environmental samples.

The present invention further provides a method for screening for inhibitors of BoNTs using the above described in vitro system. Because of its high sensitivity, rapid readout, and ease of use An in vitro systems based on the present invention is also suitable for screening toxin inhibitors. Specifically, a suitable BoNT substrate-FRET construct is exposed to a corresponding BoNT, in the presence of a candidate inhibitor substance, and changes in FRET signals are monitored to determine whether the candidate inhibits the activities of the BoNT.

The present invention further provides for a method for detecting a BoNT using a cell-based system for detecting BoNTs and further for screening for inhibitors of BoNTs. A suitable BoNT substrate-FRET construct as described above is expressed inside a cell, and the cell is then exposed to a sample suspected of containing a BoNT, and changes in FRET signals are then monitored as an indication of the presence/absence or concentration of the BoNT. Specifically, a decrease in FRET signals indicates that the sample contains a corresponding BoNT.

Cell-based high-throughput screening assays have the potential to reveal not only agents that can block proteolytic activity of the toxins, but also agents that can block other steps in the action of the toxin such as binding to its cellular receptor(s), light chain translocation across endosomal membranes and light chain refolding in the cytosol after translocation.

The present invention further provides a method for screening for inhibitors of BoNTs using the above described cell-based system. Specifically, a cell expressing a suitable BoNT substrate-FRET construct is exposed to a corresponding BoNT, in the presence of a candidate inhibitor substance, and changes in FRET signals are monitored to determine whether the candidate inhibits the activities of the BoNT. Compared to other in vitro based screening methods which can only identify direct inhibitors of toxin-substrate interaction, the cell-based screening method of the present invention further allows for the screening for inhibitors of other toxin-related activities, such as but not limited to toxin-membrane receptor binding, membrane translocation, and intra cellular toxin movement.

According to a preferred embodiment, a recombinant nucleic acid molecule, preferably an expression vector, encoding a BoNT substrate polypeptide and two suitable FRET-effecting fluorescent peptides is introduced into a suitable host cell. An ordinarily skilled person can choose a suitable expression vector, preferably a mammalian expression vector for the invention, and will recognize that there are enormous numbers of choices. For example, the pcDNA series of vectors, such as pCI and pSi (from Promega, Madison, Wis.), CDM8, pCeo4. Many of these vectors use viral promoters. Preferably, inducible promoters are used, such as the tet-off and tet-on vectors from BD Biosciences (San Jose, Calif.).

Many choices of cell lines are suitable as the host cell for the present invention. Preferably, the cell is of a type in which the respective BoNT exhibits its toxic activities. In other words, the cells preferably displays suitable cell surface receptors, or otherwise allow the toxin to be translocated into the cell sufficiently efficiently, and allow the toxin to cleave the suitable substrate polypeptide. Specific examples include primary cultured neurons (cortical neuron, hippocampal neuron, spinal cord motor neuron, etc); PC12 cells or derived PC12 cell lines; primary cultured chromaphin cells; several cultured neuroblastoma cell lines, such as murine cholinergic Neuro 2a cell line, human adrenergic SK-N-SH cell line, and NS-26 cell line. See e.g. Foster and Stringer (1999), Genetic Regulatory Elements Introduced Into Neural Stem and Progenitor Cell Populations, Brain Pathology 9: 547-567.

The coding region for the substrate-FRET polypeptide is under the control of a suitable promoter. Depending on the types of host cells used, many suitable promoters are known and readily available in the art. Such promoters can be inducible or constitutive. A constitutive promoter may be selected to direct the expression of the desired polypeptide of the present invention. Such an expression construct may provide additional advantages since it circumvents the need to culture the expression hosts on a medium containing an inducing substrate. Examples of suitable promoters would be LTR, SV40 and CMV in mammalian systems; E. coli lac or trp in bacterial systems; baculovirus polyhedron promoter (polh) in insect systems and other promoters that are known to control expression in eukaryotic and prokaryotic cells or their viruses. Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), .alpha.-amylase (amy), amyloglucosidase (AG— from the glaA gene), acetamidase (amdS) and glyceraldehyde-3-phosphate dehydrogenase (gpd) promoters. Examples of strong yeast promoters are those obtainable from the genes for alcohol dehydrogenase, lactase, 3-phosphoglycerate kinase and triosephosphate isomerase. Examples of strong bacterial promoters include SPO.sub.2 promoters as well as promoters from extracellular protease genes.

Hybrid promoters may also be used to improve inducible regulation of the expression construct. The promoter can additionally include features to ensure or to increase expression in a suitable host. For example, the features can be conserved regions such as a Pribnow Box or a TATA box. The promoter may even contain other sequences to affect (such as to maintain, enhance or decrease) the levels of expression of the nucleotide sequence of the present invention. For example, suitable other sequences include the Shl-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat, 1987, Gene 217: 217-225; and Dawson, 1993, Plant Mol. Biol. 23: 97).

The expression vector may also contain sequences which act on the promoter to amplify expression. For example, the SV40, CMV, and polyoma cis-acting elements (enhancer) and a selectable marker can provide a phenotypic trait for selection (e.g. dihydrofolate reductase or neomycin resistance for mammalian cells or amplicillin/tetracyclin resistance for E. coli). Selection of the appropriate vector containing the appropriate promoter and selection marker is well within the level of those skilled in the art.

Preferably the coding region for the substrate-FRET polypeptide is under the control of an inducible promoter. In comparison to a constitutive promoter, an inducible promoter is preferable because it allows for suitable control of the concentration of the reporter in the cell, therefore the measurement of changes in FRET signals are greatly facilitated.

For example, FRET reporter can be controlled using the Tet-on & Tet-off system (BD Biosciences, San Jose, Calif.). Under the control of this promoter, gene expression can be regulated in a precise, reversible and quantitative manner. Briefly, for Tet-on system, the transcription of downstream gene only happens when doxycycline is present in the culture medium. After the transcription for a certain period of time, we can change culture medium to deplete doxycycline, thus, stop the synthesis of new FRET reporter proteins. Therefore, there is no background from newly synthesized FRET proteins, and we may be able to see a faster change after toxin treatment.

Fluorescent analysis can be carried out using, for example, a photon counting epifluorescent microscope system (containing the appropriate dichroic mirror and filters for monitoring fluorescent emission at the particular range), a photon counting photomultiplier system or a fluorometer. Excitation to initiate energy transfer can be carried out with an argon ion laser, a high intensity mercury (Hg) arc lamp, a fiber optic light source, or other high intensity light source appropriately filtered for excitation in the desired range. It will be apparent to those skilled in the art that excitation/detection means can be augmented by the incorporation of photomultiplier means to enhance detection sensitivity. For example, the two photon cross correlation method may be used to achieve the detection on a single-molecule scale (see e.g. Kohl et al., Proc. Nat'l. Acad. Sci., 99:12161, 2002).

A number of parameters of fluorescence output may be measured. They include: 1) measuring fluorescence emitted at the emission wavelength of the acceptor (A) and donor (D) and determining the extent of energy transfer by the ratio of their emission amplitudes; 2) measuring the fluorescence lifetime of D; 3) measuring the rate of photobleaching of D; 4) measuring the anisotropy of D and/or A; or 5) measuring the Stokes shift monomer/excimer fluorescence. See e.g. Mochizuki et al., (2001) "Spatio-temporal images of grow-factor-induced activation of Ras and Rap1." Nature 411:1065-1068, Sato et al. (2002) "Fluorescent indicators for imaging protein phosphorylation in single living cells." Nat. Biotechnol. 20:287-294.

In another embodiment, the present invention provides a method for detecting BoNTs using surface plasmon resonance imaging (SPRi) techniques. Surface plasmon resonance (SPR) is an established optical technique for the detection of molecular binding, based on the generation of surface plasmons in a thin metal film (typically gold) that supports the binding chemistry. Surface plasmons are collective oscillations of free electrons constrained in the metal film. These electrons are excited resonantly by a light field incident from a highly refractive index prism. The angle of incidence q over which this resonant excitation occurs is relatively narrow, and is characterized by a reduction in the intensity of the reflected light which has a minimum at the resonant angle of incidence qr. The phase of the reflected light also varies nearly linearly with respect to q in this region. The value of qr is sensitive to the refractive index of the medium that resides within a few nanometers of the metal film. Small variations in the refractive index, due to the binding of a molecule to the film, or due to the change in the molecular weight of the bound molecules, may therefore be detected as a variation of this angle. Many methods are known in the art for anchoring biomolecules to metal surfaces, for detecting such anchoring and measuring SPRi are known in the art, see e.g. U.S. Pat. No. 6,127,129 U.S. Pat. No. 6,330,062, and Lee et al., 2001, Anal. Chem. 73: 5527-5531, Brockman et al., 1999, J. Am. Chem. Soc. 121: 8044-8051, and Brockman et al., 2000, Annu Rev. Phys. Chem. 51: 41-63, which are all incorporated herein by reference in their entirety.

In practice a layer of BoNT target peptides may be deposited on the metal. A sample suspected of containing a corresponding BoNT is applied to the composite surface, and incubated to allow the toxin, if present, to cleave the bound target peptides. The cleavage will result in the decrease of the molecular weight of the peptide bound to the metal surface, which decrease can then be detected using standard equipments and methods. A decrease in the thickness of the bound layer indicates that cleavage has occurred and in consequence, the sample contains the toxin corresponding to the target peptide.

Alternatively, binding of a BoNT protein to its corresponding substrate peptide, which is anchored to the metal surface, will also cause a change in the refractive index and can be detected by known SPRi techniques and apparati.

Many methods are known in the art for anchoring or depositing protein or peptides molecules on to a metal surface. For example, add an extra Cys residue can be added to the end of the peptide, which can then be crosslinked onto the metal surface. Indirectly, an antibody can be anchored first to the metal surface, and to which antibody the toxin substrate can be bound. Indirect anchoring via antibodies is suitable for the present invention so long as the antibody-substrate binding does not prevent the toxin from recognizing and accessing the cleavage site of the substrate. Furthermore, nickel-NTA or glutathione that can be used to hold down his6 or GST fusion proteins, respectively. Additional information regarding anchoring peptide to metal surface may be found in Wegner et al, (2002) Characterization and Optimization of Peptide Arrays for the Study of pitope-Antibody Interactions Using Surface Plasmon Resonance Imaging" Analytical Chemistry 74:5161-5168, which is also incorporated herein by reference in its entirety.

Changes of about 10-16 bases in a nucleic acid molecule, corresponding to 3,000 to 6,400 d in molecular weight, can be easily detected by SPRi. This implies that a change of as few as 16 amino acid residues in a peptide molecule can be detected. This high sensitivity allows the anchoring of a short peptide substrate onto the surface, instead of using the full-length toxin substrate proteins. Short peptide fragments are preferred because they are more stable, less expensive to prepare and allow higher reaction specificity.

EXAMPLES

Materials and Methods

Construction of bio-sensor DNA constructs: YFP cDNA (Clontech) was inserted into the pECFP-C1 vector (Clontech) using EcoRI and BamHI site to generate pECFP-YFP vector. cDNA encoding amino acid 33-94 of rat syb II was amplified using PCR and into pECFP-YFP vector using XhoI and EcoRI sites, which are between CFP and YFP gene, to generate CFP-SybII-YFP (also referred to as CFP-Syb (33-94)-YFP) construct that can be used to transfect cells. Construct CFP-SNAP-25-YFP (also referred to as CFP-SNAP-25 (141-206)-YFP) was built using the same method, but using residues 141-206 of SNAP-25. A construct (CFP-SNAP25FL-YFP) with full-length rat SNAP-25B as the linker was also made. In order to purify recombinant chimera proteins using bacteria *E. coli*, we also moved CFP-SybII-YFP gene and CFP-SNAP-25-YFP gene from pECFP-YFP vector into a pTrc-his (Invitrogen) vector using NheI and BamHI sites.

The mutation of four Cys residues of SNAP-25 to Ala was accomplished by site-directed mutagenesis using PCR, and the fragment was then inserted between CFP and YFP as described above. SNAP-25(83-120)-CFP-SNAP-25(141-206)-YFP were built by first inserting the cDNA fragment that encoding the residues 83-120 of SNAP-25 into the XhoI/EcoRI sites of pEYFP-N1(Clontech), and then subcloning CFP-SNAP-25(141-206) cDNA into downstream sites using EcoRI/BamHI. YFP-Syb(FL)-CFP was built by first inserting a full length Syb II cDNA into pECFP-C1 vectors at EcoRI and BamHI sites, and then inserting a full length YFP cDNA into the upstream at XhoI and EcoRI sites. YFP-Syb(33-116)-CFP was built by replacing full-length Syb in YFP-Syb(FL)-CFP construct via EcoRI/BamHI sites. All cDNA fragments were generated via PCR.

Protein purification and fluorescence spectra acquisition: His$_6$-tagged CFP-SybII-YFP and CFP-SNAP-25-YFP proteins were purified as described (Chapman et al., A novel function for the second C2 domain of synaptotagmin. Ca$^{2+}$-triggered dimerization. J. Biol. Chem. 271, 5844-5849 (1996)). Proteins were dialyzed using HEPES buffer (50 mM HEPES, pH 7.1) overnight. 300 nM protein was put into a cuvette in a total volume of 500 $\mu$l HEPES buffer that contains 2 mM DTT and 10 $\mu$M ZnCl$_2$. The emission spectra from 450 nM to 550 nM was collected using a PTIQM-1 fluorometer. The excitation wavelength is 434 nM, which is the optimal excitation wavelength for CFP.

Activation of *Botulinum* neurotoxin and monitoring the cleavage of bio-sensor proteins: BoNT/A, B, E or F was incubated with 2 mM DTT and 10 $\mu$M ZnCl$_2$ for 30 min at 37.degree. C. to reduce the toxin light chain from the heavy chain. For experiments using a PTIQM-1 fluorometer, 10 nM BoNT/A, E, or 50 nM BoNT/B, F were added into the cuvette that contains 300 nM corresponding FRET sensors. The emission spectra were collected as described above, at certain time intervals after adding toxins (e.g. 0, 2, 5, 10, 30, 60, 90 min). At the end of each emission scan, a small portion of the sample (30 $\mu$l) was collected, mixed with SDS-loading buffer, and later subjected onto a SDS-page gel. The sensor protein and the cleavage products were visualized with an anti-his$_6$ antibody using enhanced chemiluminescence (ECL) (Pierce).

For experiments using a spectrofluorometer, 300 nM FRET sensor protein were prepared in a 100 $\mu$l volume per well in a 96-well plate. Various concentrations of BoNTs were added into each well, and samples were excited at 434 nM. The emission spectra of YFP channel (527 nM), and CFP channel (470 nM) were collected for 90 min at 30 sec interval. The FRET ratio is determined by the ratio between YFP channel and CFP channel for each data point.

Measure the FRET ratio change in live cells after toxin treatment DNA constructs pECFP-SNAP25-YFP were used to transfect PC12 cells using electroporation (Bio-Rad). Cells were passed 24 hrs. after the transfection, and 50 nM BoNT/A were added into the culture medium. After incubation for 72 hours with toxin, the fluorescence images of cells that express FRET sensor were collected using a Nikon TE-300 microscope. Two images of each cell (CFP channel and FRET channel) were collected using the following filter set (Chroma Inc.): CFP channel: CFP excitation filter (436/10 nm), JP4 beamsplitter, CFP emission filter: (470/30 nm); FRET channel: CFP excitation filter (436/10 nm), JP4 beamsplitter, YFP emission filter (535/30 nm). The background (the areas that contain no cells) was subtracted from each image, and the fluorescence intensities of CFP channel and FRET channel of each cell were compared using MetaMorph software. The FRET ratio is determined by the intensity ratio between FRET channel and CFP channel as previous described. Control cells were not treated with toxins but were analyzed in an identical manner. To test BoNT/B in live cells, we transfected a PC12 cell line that express syt II using the same procedure as described above.

Live cell imaging and FRET analysis: PC12 cells were transfected with various cDNA constructs indicated in the Figure legends via electroporation (Bio-Rad, CA). The fluorescence images were collected using a Nikon TE-300 microscope with a 100.times. oil-immersed objective. CFP/YFP FRET in live cells was quantified using an established method with the three-filter set method (Gordon et al., Quantitative fluorescence resonance energy transfer measurements using fluorescence microscopy. Biophys J. 74, 2702-2713 (1998); Sorkin et al., Interaction of EGF receptor and grb2 in living cells visualized by fluorescence resonance energy transfer (FRET) microscopy. Curr. Biol. 10, 1395-1398 (2000)). In brief, three consecutive images were acquired for each cell, through three different filter sets: CFP filter (excitation, 436/10 nm; emission, 470/30 nm), FRET filter (excitation, 436/10 nm; emission, 535/30 nm), and YFP filter (excitation, 500/20 nm, emission, 535/30 nm). A JP4 beam splitter (Set ID 86000, Chroma Inc. VT) was used. All images were acquired with exact the same settings (4.times.4 Binning, 200 ms exposure time). In order to exclude the concentration-dependent FRET signal that can arise from high expression level of fluorescence proteins, only cells with CFP and YFP intensities below the half value of the maximal 12-bit scale (1-2097 gray scale) were counted in our experiments (Miyawaki et al., Monitoring protein conformations and interactions by fluorescence resonance energy transfer between mutants of green fluorescent protein. Methods Enzymol. 327, 472-500 (2000); Erickson et al., DsRed as a potential FRET partner with CFP and GFP. Biophys J 85, 599-611 (2003)). The background (from areas that did not contain cells) was subtracted from each raw image before FRET values were calculated. The fluorescence intensity values of each image were then obtained and compared. PC12 cells transfected with CFP or YFP alone were first tested in order to obtain the crosstalk value for these filter sets. The FRET filter channel exhibits about 56-64% of bleed-through for CFP, and about 24% for YFP. There is virtually no crosstalk for YFP while using the CFP filter, or for CFP while using the YFP filter, which greatly simplified the FRET calculations. For cells expressing toxin sensors, the "corrected FRET" value was calculated using the following equation: corrected FRET=FRET−(CFP.times.0.60)−(YFP.times.0.24), where FRET, CFP and YFP correspond to fluorescence intensity of images acquired through FRET, CFP and YFP filter sets, respectively. The average fraction of bleed-through coming from CFP and YFP fluorescence are 0.6 and 0.24, respectively, when acquiring image through the FRET filter set. Because toxin cleavage of the CFP-SNAP25FL-YFP sensor resulted in the membrane dissociation of YFP fragment, which was degraded in the cytosol (FIG. 7c, e), the FRET ratio used in our data analysis is calculated as normalizing "corrected FRET" value to only the CFP fluorescence intensity (corrected FRET/CFP). We note that the CFP intensity in these calculations was an underestimate due to donor quenching if FRET occurred. However, it has been reported the decrease in CFP fluorescence because of donor quenching is only about 5-10% (Gordon et al., Quantitative fluorescence resonance energy transfer measurements using fluorescence microscopy. Biophys J 74, 2702-2713 (1998); Sorkina et al., Oligomerization of dopamine transporters visualized in living cells by fluorescence resonance energy transfer microscopy. J. Biol. Chem. 278, 28274-28283 (2003)). All images and calculations were performed using MetaMorph software (Universal Imaging Corp., PA).

For experiments involving toxin treatment, indicated holotoxins were added to the cell culture media for various time, and cells were then analyzed as described above. Control cells were transfected with toxin sensors but not treated with toxins, and they were analyzed in an identical manner.

Immunoblot analysis of toxin substrate cleavage: Wild type PC12 cells or Syt II+PC12 cells (Dong et al., 2003, supra) were transfected with various toxin sensor cDNA constructs as indicated in the Figure legends. BoNT/A or B was added to the culture medium 24 h after transfection and cells were incubated for another 48 hrs. Cells were then harvested and cell lysates were subject to immunoblot analysis as described previously. Control cells were transfected with the same cDNA constructs and assayed in parallel except they were not treated with toxins. One third of the control cell lysates were treated with toxins in vitro (200 nM BoNT/A or B, 30 min at 37.degree. C.), and subjected to immunoblot analysis. Endogenous SNAP-25 and transfected CFP-SNAP-25-YFP sensors were assayed using an anti-SNAP-25 antibody 26. CFP-SNAP-25-YFP and CFP-SybII-YFP sensor proteins were also assayed using a GFP polyclonal antibody (Santa Cruz., CA). An anti-his6 antibody (Qigen Inc., CA) was used to assay for recombinant sensor protein cleavage.

Example 1

Bio-Sensors Based on CFP-YFP FRET Pair and *Botulinum* Neurotoxin Protease Activity In order to monitor *botulinum* neurotoxin protease activity using FRET method, CFP and YFP protein are connected via syb II or SNAP-25 fragment, denoted as CFP-SybII-YFP and CFP-SNAP-25-YFP, respectively (FIG. 1A). Short fragments of toxin substrates were used instead of the full-length protein to optimize the CFP-YFP energy transfer efficiency, which falls exponentially as the distance increases. However, the cleavage efficiency by BoNTs decreases significantly as the target protein fragments get too short. Therefore, the region that contain amino acid 33-96 of synaptobrevin sequence was used because it has been reported to retain the same cleavage rate by BoNT/B, F, and TeNT as the full length synaptobrevin protein does. Similarly, residues 141-206 of SNAP-25 were selected to ensure that the construct can still be recognized and cleaved by BoNT/A and E.

The FRET assay is depicted in FIG. 1B. When excited at 434 nM (optimal excitation wavelength for CFP), the CFP-SybII-YFP and CFP-SNAP-25-YFP chimera protein would elicit YFP fluorescence emission because of the FRET between CFP-YFP pair. *Botulinum* neurotoxins can recognize and cleave the short substrate fragments between CFP and YFP, and FRET signal will be abolished after CFP and YFP are separated. Because these chimera proteins can be expressed in living cells, they are also denoted as "bio-sensor" for *botulinum* neurotoxins.

We first purified his.sub.6-tagged recombinant chimera protein of CFP-SybII-YFP, and CFP-SNAP-25-YFP, and characterized their emission spectra using a PTIQM-1 fluorometer. As expected, both bio-sensor proteins show an obvious YFP fluorescence peak at 525 nM when their CFP were excited at 434 nM (FIG. 2B, C). On the contrary, the YFP alone only gave small fluorescence signal when excited directly at 434 nM (FIG. 2A). The mixture of individual CFP and YFP doesn't have the peak emission at 525 nM (FIG. 2A). This demonstrated the YFP fluorescence peak observed using bio-sensor proteins resulted from FRET. Because the FRET ratio (YFP fluorescence intensity/CFP fluorescence intensity) was affected by many factors, such as buffer composition, the Zn.sup.2+ concentration and the concentration of reducing agents (data not shown), the experiments thereafter were all carried out in the same buffer conditions (50 mM Hepes, 2 mM DTT, 10.mu.M ZnCl.sub.2, pH 7.1). 2 mM DTT and 10.mu.M Zn.sup.2+ were added to optimize the *botulinum* neurotoxin protease activity.

Example 2

Figure 3:
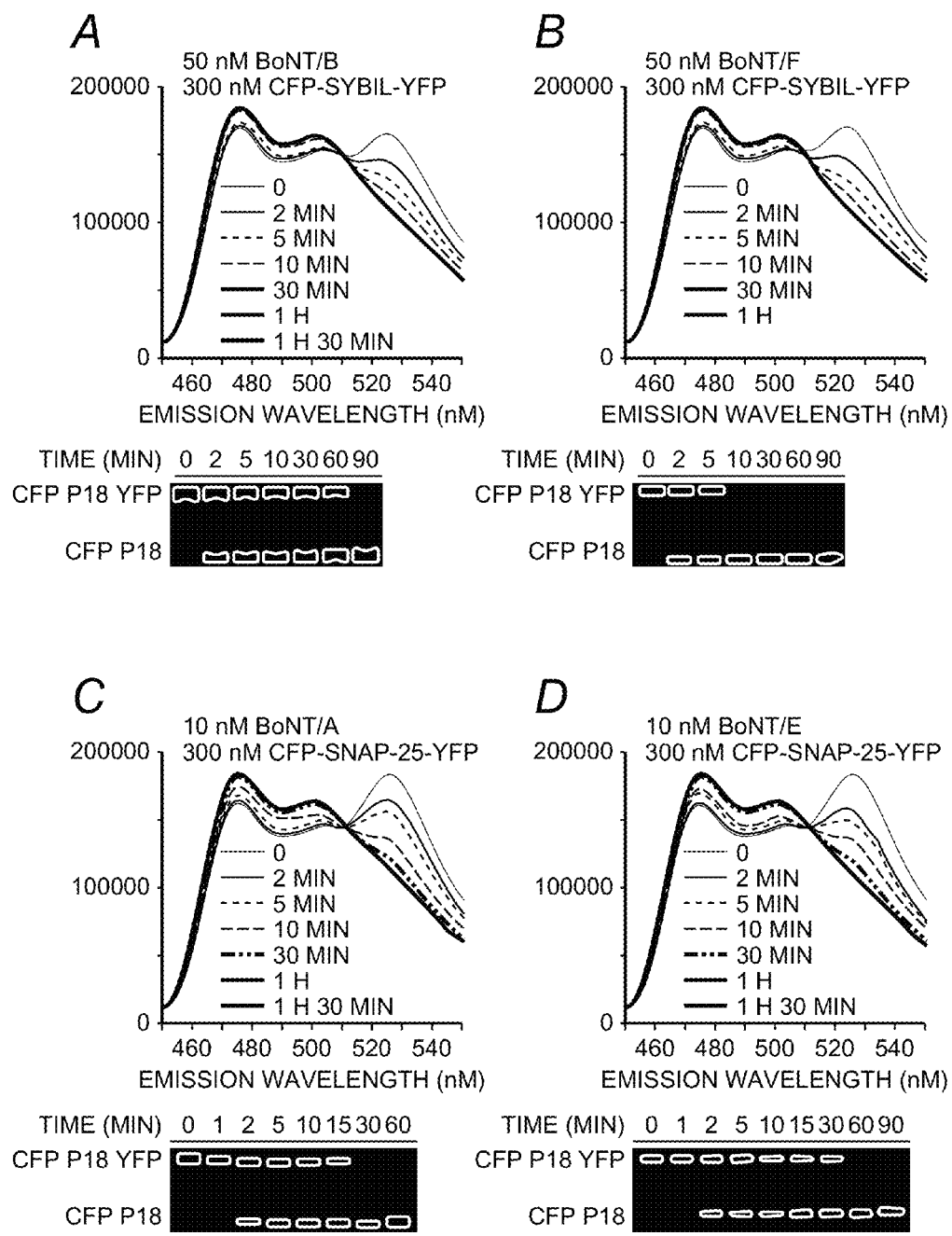
FIG. 3 depicts that the cleavage of bio-sensor proteins by *botulinum* neurotoxin can be monitored by emission spectra scan in real time in vitro. A): BoNT/B were pre-reduced with 2 mM DTT, 10 $\mu$M ZnCl$_2$ for 30 min at 37 $^\circ$C. 50 nM toxin were added into a cuvette that contained 300 nM CFP-SybII-YFP protein in the Hepes buffer (50 mM Hepes, 2 mM DTT, 10 $\mu$M ZnCl$_2$). The emission spectra was recorded as described in FIG. 2A at indicated time before and after adding toxin (upper panel). 30 $\mu$l samples were taken from the cuvette after each emission scan, and mixed with SDS-loading buffer. These samples were subject to SDS-page and enhanced chemilluminescence (ECL). The cleavage of CFP-SybII-YFP fusion protein was detected using an anti-his$_6$ antibody that recognizes the his$_6$ tag at the fusion protein N-terminus (lower panel). The cleavage of CFP-SybII-YFP fusion protein resulted in decreased YFP fluorescence and increased CFP fluorescence. This change was recorded in real-time by emission spectra scan. B): CFP-SybII-YFP was used to test BoNT/F activity, as described in panel A. C): CFP-SNAP-25-YFP was used to test BoNT/A activity (10 nM toxin was used), as described in panel A. D): CFP-SNAP-25-YFP was used to test BoNT/E activity (10 nM toxin was used), as described in panel A.

Monitoring the Cleavage of Bio-Sensor Proteins by *Botulinum* Neurotoxins In Vitro 300 nM chimera protein CFP-SybII-YFP was mixed with 50 nM pre-reduced BoNT/B holotoxin in a cuvette. The emission spectra were collected at different time points after adding BoNT/B (0, 2, 5, 10, 30, 60 min, etc). At the end of each scan, a small volume of sample (30.mu.1) was taken out from the cuvette and mixed with SDS-loading buffer. These samples later were subjected to SDS-page gels and the cleavage of chimera proteins were visualized using an antibody against the his.sub.6 tag in the recombinant chimera protein. As shown in FIG. 3A, the incubation of bio-sensor protein with BoNT/B resulted in a decrease of YFP emission and increase of CFP emission. The decrease of FRET ratio is consistent with the degree of cleavage of the chimera protein by BoNT/B (FIG. 3A, low panel). This result demonstrates the cleavage of the bio-sensor protein can be monitored in real time by recording the change in its FRET ratio.

The same assay was performed to detect CFP-SybII-YFP cleavage by BoNT/F, and CFP-SNAP-25-YFP cleavage by BoNT/A or E (FIG. 3B, C, D). Similar results were obtained with the experiment using BoNT/B. IN all cases, we observed the same kinetics of cleavage of the substrate using both the optical readout and the immunoblot blot analysis. BoNT/A and E cleaved their chimera substrate much faster than BoNT/B and F did in our assay. Thus, only 10 nM BoNT/A or E were used in order to record the change occurred within first several minutes. The cleavage of chimera protein is specific, since mixing BoNT/B and F with CFP-SNAP-25-YFP, or mixing BoNT/A and E with CFP-SybII-YFP did not result in any change in FRET ratio or substrate cleavage (data not shown).

Example 3

Figure 4:
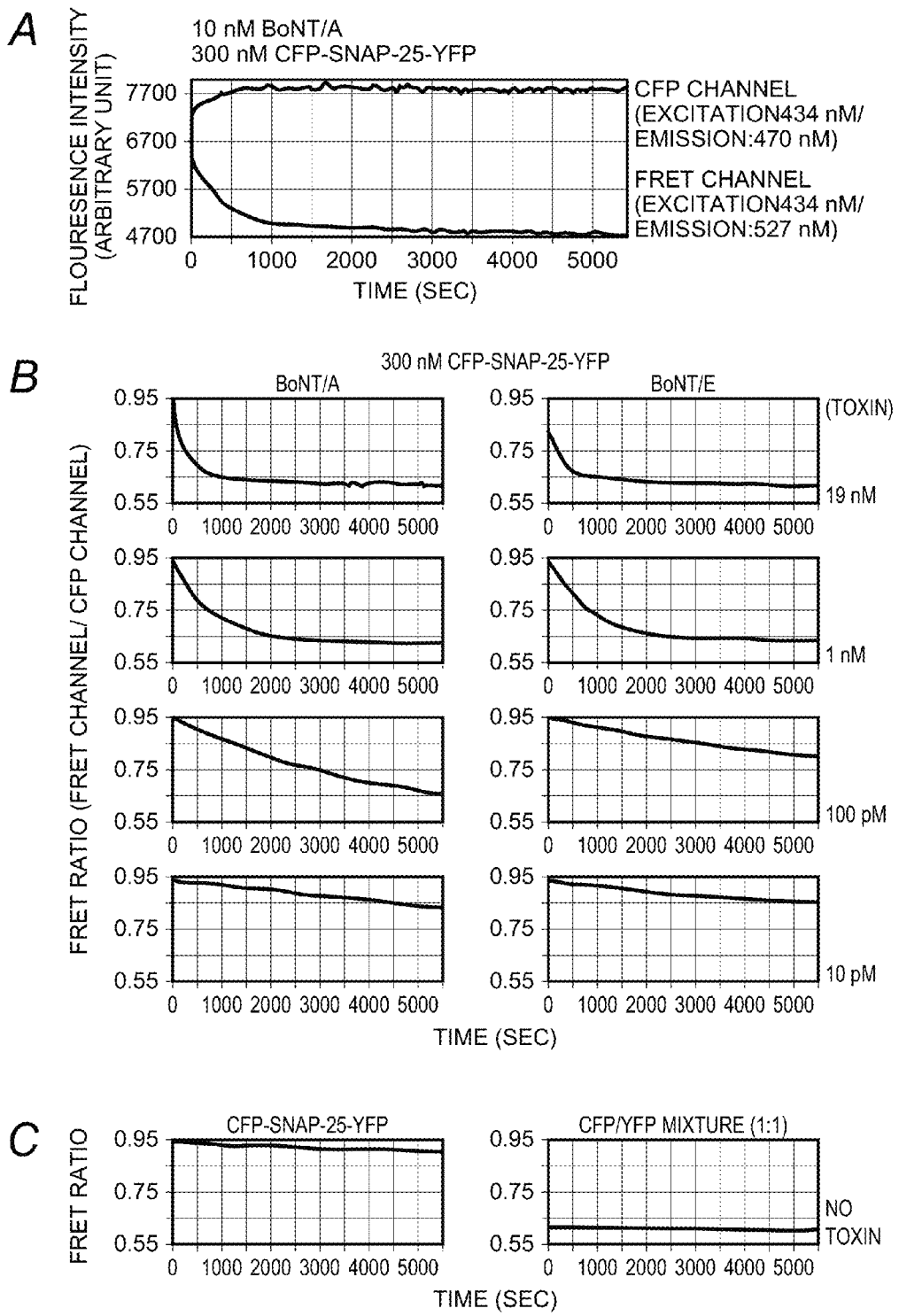
FIG. 4 shows the monitoring of *botulinum* neurotoxin protease kinetics using bio-sensor proteins in a microplate spectrofluorometer. A): Fluorescence change during the cleavage of bio-sensor proteins by *botulinum* neurotoxin could be recorded in real time using a plate-reader. 10 nM BoNT/A were mixed with 300 nM CFP-SNAP-25-YFP, and 100 $\mu$l per well sample was scanned using a plater-reader. The excitation is 434 nm, and for each data point, both emission value at 470 nm (CFP channel), and 527 nm (YFP or FRET channel) were collected. The reaction was traced for one and half hour at the interval of 30 sec per data point. The decrease of YFP fluorescence and the increase of CFP fluorescence were monitored in real time. B): The rate of cleavage is dependent on the concentration of the neurotoxin. The various concentrations of *botulinum* neurotoxin A and E were tested for their ability to cleave the same amount of bio-sensor proteins. FRET signal change (FRET ratio) is measured by the ratio between YFP emission signal and the CFP emission signal at the same data point. C): CFP-SNAP-25-YFP protein alone, and the CFP/YFP protein mixture (1:1) were scanned at the same time, as the internal control.

Monitoring *Botulinum* Neurotoxin Protease Activity in Real Time Using a Microplate Spectrofluorometer The above experiments demonstrated that the activity of *botulinum* neurotoxin can be detected in vitro by monitoring the changes of the emission spectra of their target bio-sensor proteins. We then determined if we could monitor the cleavage of bio-sensor proteins in real time using a microplate reader—this will demonstrate the feasibility to adapt this assay for future high-throughput screening. As shown in FIG. 4A, 300 nM CFP-SNAP-25-YFP chimera protein was mixed with 10 nM BoNT/A in a 96-well plate. CFP was excited at 436 nm and the fluorescence of the CFP channel (470 nM) and YFP channel (527 nM) were recorded over 90 min at 30 sec intervals. Addition of BoNT/A resulted in the decrease of YFP channel emission and the increase of CFP channel emission. This result enabled us to trace the kinetics of *botulinum* neurotoxin enzymatic activity in multiple samples in real time. For instance, as shown in FIG. 4B, various concentration of BoNT/A or E were added into 300 nM CFP-SNAP-25-YFP, and the FRET ration of each sample were monitored simultaneously as described in FIG. 4A. Changes in the FRET ratio were related to the toxin concentration—higher toxin concentration resulted in faster decrease of the FRET ratio. This change in FRET ratio is specific, because no significant change was detected for either CFP-SNAP-25-YFP alone (FIG. 4C left panel) or a mixture of CFP and YFP (FIG. 4C right panel).

Although it would be difficult to correlate the FRET ratio change with the actual cleavage of the bio-sensor proteins at this stage, this method still provides the easiest way to compare toxin cleavage kinetics among multiple samples when these samples were prepared and scanned simultaneously—it is particularly useful for high throughput screening toxin inhibitors because it would provide information about how the inhibitor affects toxin enzymatic activities. We note that the unit for each kinetic parameter would be the FRET ratio instead of substrates concentration in these cases.

The sensitivity of this FRET based assay is determined by incubating various concentrations of toxins with fixed amount of their target bio-sensor proteins for certain period of time. The FRET ratio is recorded using a microplate spectrofluorometer, and plotted against toxin concentration. As shown in FIG. 5A, this method has similar sensitivities for BoNT/A and E after 4 hours incubation (EC50 for BoNT/A is 15 pM, and for BoNT/E is 20 pM, upper panel), and incubation for 16 hours slightly increased the detection sensitivity (FIG. 5A, lower panel). The sensitivities for BoNT/B and F are close to each other, but are about 10 times lower than BoNT/A and E with 4 hours incubation (FIG. 5B, upper panel, EC50 is 242 pM for BoNT/B, and 207 pM for BoNT/F). Extension of the incubation period to 16 hours increased the ability to detect BoNT/B and BoNT/F activity by 8-fold and 2-fold, respectively.

Example 4

Monitoring *Botulinum* Neurotoxin Activity in Live Cells

CFP-YFP based bio-sensor assay not only can be used to detect *botulinum* neurotoxin in vitro, but also can be used in live cells. To establish this application, PC 12 cells were transfected with CFP-SNAP-25-YFP. PC12 cell is a neuroendocrine cell line that is able to take up BoNT/A and E. Transfected cells were incubated with BoNT/A (50 nM) for 72 hours, and the FRET ratio of cells that express CFP-SNAP25-YFP were recorded using a epi-fluorescence microscope equipped with special filter sets for CFP-YFP FRET detection. Briefly, the FRET ratio is calculated as the ratio between the fluorescence intensity of the images from the same cell collected using two filter sets, one for CFP (excitation 437 nm/emission 470 nm), and another for FRET (excitation 437 nm/emission 535 nm). A total number of 53 cells were collected, and compared to the same number of control cells which express the same bio-sensor protein but were not exposed to toxin. As shown in FIG. 6A, BoNT/A treatment for 72 hours significantly decreased FRET ratio for the cell population that was examined ($p<1.47E-05$). Wild type PC12 cells are not sensitive to BoNT/B and F.

A PC12 cell line was recently created that expresses both synaptotagmin II, a receptor for BoNT/B, and CFP-SybII-YFP bio-sensor. These cells were used to detect BoNT/B action in live cells. As shown in FIG. 6B, BoNT/B (30 nM) treatment for 72 hours significantly decreased FRET ratio of the bio-sensor proteins expressed in cells ($p<2.1E-10$). We note that there were still large number of cells that do not appear to change FRET ratio for both bio-sensor proteins. There are several possible explanations. First, the toxin/bio-sensor protein ratio may be too low in these cells, thus, the significant cleavage of bio-sensor proteins may require a longer incubation time. Second, these cells may have high level of protein synthesis activity, thus new bio-sensor protein was synthesis quickly to replace cleavage products. Nevertheless, these experiments demonstrate the feasibility to adopt this FRET based assay in living cells and neurons.

Example 5

Cell Based Detection of BoNTs

Figure 2:
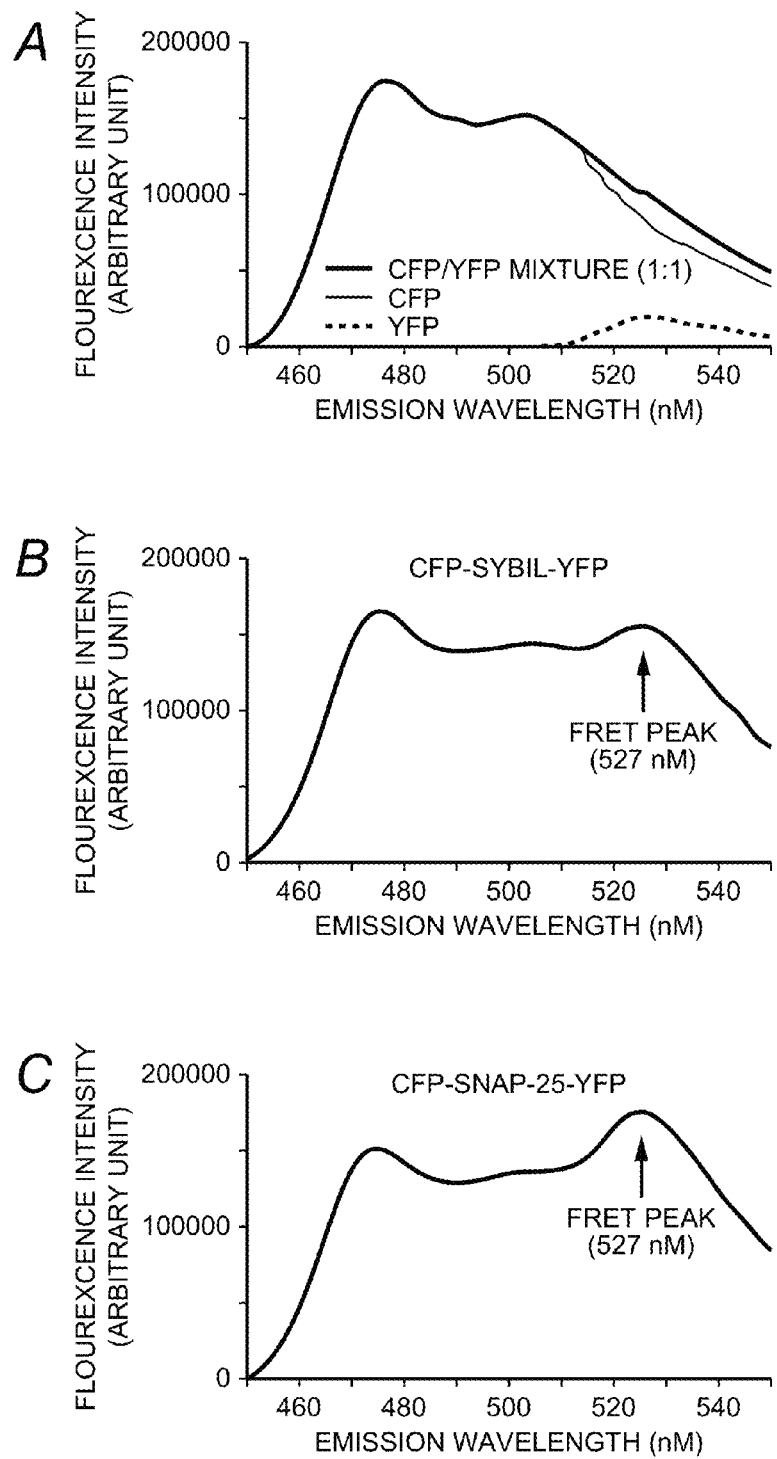
FIG. 2 shows the fluorescence emission spectra of the recombinant bio-sensor proteins.

To carry out cell-based studies, we first transfected PC12 cells with CFP-SNAP-25(141-206)-YFP sensor (FIG. 7a). The FRET signal in living cells was acquired using an established three-filter set method with an epi-fluorescence microscope as shown in FIG. 2a (Gordon, et al., Quantitative fluorescence resonance energy transfer measurements using fluorescence microscopy. Biophys. J. 74, 2702-2713 (1998); and Sorkin et al., Interaction of EGF receptor and grb2 in living cells visualized by fluorescence resonance energy transfer (FRET) microscopy. Curr. Biol. 10, 1395-1398 (2000), as described above in the Materials and Methods Section. Transfected PC12 cells were treated with 50 nM BoNT/A for 96 hrs. Their fluorescence images were analyzed and the normalized FRET ratio (corrected FRET/CFP) was plotted in FIG. 7b. Although SNAP-25(141-206) fragments were reported to have similar toxin cleavage rates as full length SNAP-25 in vitro (Washbourne et al., *Botulinum* neurotoxin types A and E require the SNARE motif in SNAP-25 for proteolysis. FEBS Lett. 418, 1-5 (1997)), CFP-SNAP-25 (141-206)-YFP appeared to be a poor toxin substrate in living cells. Incubation of BoNT/A (50 nM) for 96 hr exhibited a small (but significant) shift in the FRET ratio among the cell population, indicating the cleavage is inefficient in cells, and this sensor is not practical for toxin detection in cells.

Figure 8:
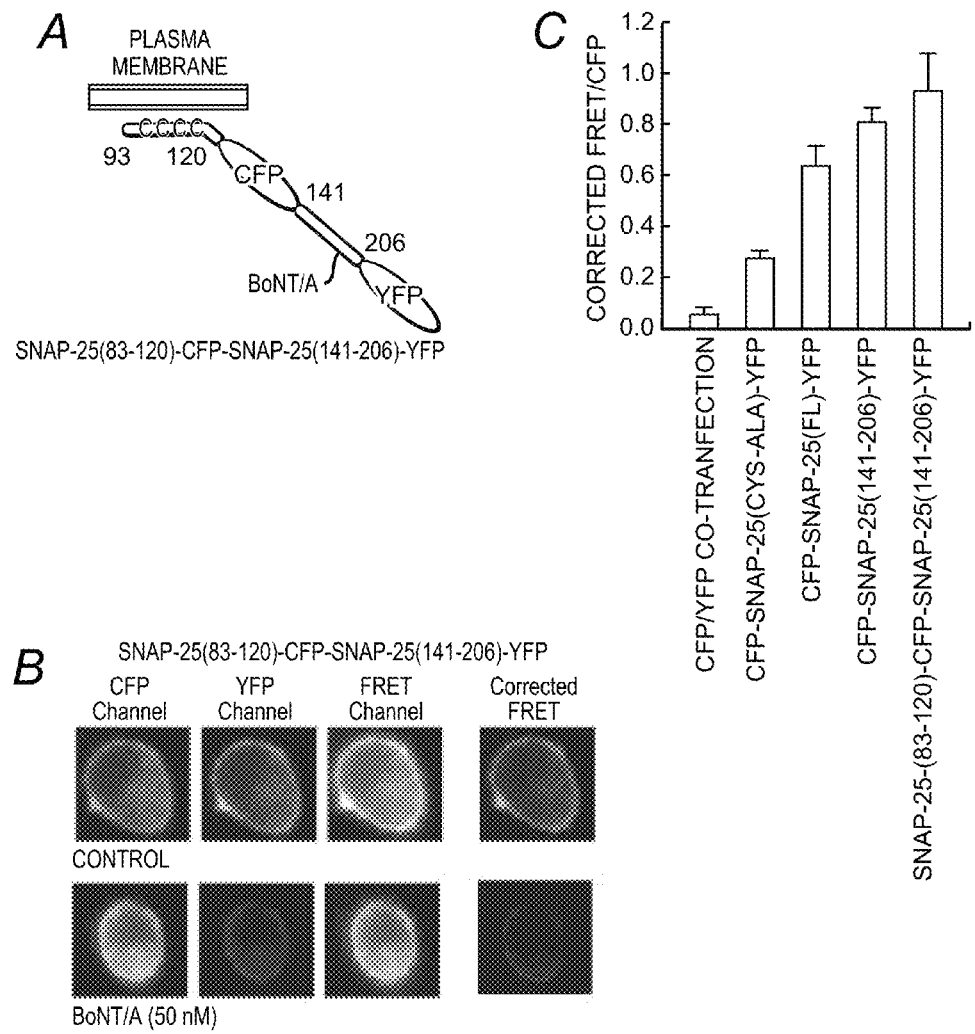
FIG. 8 shows that anchoring CFP-SNAP-25(141-206)-YFP sensor to the plasma membrane created a sensor that was efficiently cleaved by BoNT/A in cells. (a). A schematic description of the construct built to target CFP-SNAP-25(141-206)-YFP to the plasma membrane. A fragment of SNAP-25 that contains the palmitoylation sites (residues 83-120) was fused to the N-terminus of the CFP-SNAP-25(141-206)-YFP sensor, and this fragment targeted the fusion protein to the plasma membrane. (b). PC12 cells were transfected with SNAP-25(83-120)-CFP-SNAP-25(141-206)-YFP. Fifty nM BoNT/A holotoxin was added to the culture medium and the FRET signals of 80 cells were analyzed after 96 hours as described in FIG. 7a. Control cells, transfected with toxin sensors but not treated with toxins, were analyzed in parallel. The images of representative cells are shown in the left panel. This sensor yielded significant FRET (upper "corrected FRET" frame of the left panel). The FRET signal was reduced after cells were treated with BoNT/A (96 h, lower "corrected FRET" frame of the left panel). Right panel: the FRET ratios of cells are plotted as a histogram with indicated bins as described in FIG. 7b. (c). PC12 cells were transfected with various CFP/YFP constructs and the corresponding FRET ratios were determined as described in FIG. 7a. Co-expression of CFP and YFP in cells, did not result in significant FRET under our assay conditions. CFP-SNAP-25(FL)-YFP exhibited significant levels of FRET whereas the soluble CFP-SNAP-25(Cys-Ala)-YFP did not.

Surprisingly, we found that using full length SNAP-25 as the linker between CFP and YFP yielded significant levels of FRET when expressed in PC12 cells, despite the fact that SNAP-25 is 206 amino acid residues long (FIGS. 7c, and 8c). This FRET signal is dependent on the membrane anchor of SNAP-25 since mutation of the palmitoylation sites within SNAP-25 (Cys 85, 88, 90, 92 Ala) (Lane & Liu, Characterization of the palmitoylation domain of SNAP-25. J. Neurochem. 69, 1864-1869 (1997); Gonzalo et al., SNAP-25 is targeted to the plasma membrane through a novel membrane-binding domain. J. Biol. Chem. 274, 21313-21318 (1999); Koticha et al., Plasma membrane targeting of SNAP-25 increases its local concentration and is necessary for SNARE complex formation and regulated exocytosis. J. Cell Sci. 115, 3341-3351 (2002); Gonelle-Gispert et al., Membrane localization and biological activity of SNAP-25 cysteine mutants in insulin-secreting cells. J. Cell Sci. 113 (Pt 18), 3197-3205 (2000)), which results in the cytosolic distribution of the protein (denoted as CFP-SNAP-25(Cys-Ala)-YFP), significantly reduced the FRET signal (FIG. 7d). This finding suggests the membrane anchoring of SNAP-25 may result in conformational changes that bring N-terminus and C-terminus of SNAP-25 close to each other. This sensor is denoted as CFP-SNAP-25(FL)-YFP. Incubation of cells that express CFP-SNAP-25(FL)-YFP with 50 nM BoNT/A resulted in a progressive decrease in the FRET ratio over time (FIG. 7c, right panel). BoNT/A cleavage of the sensor resulted in two fragments: an N-terminal fragment of SNAP-25 tagged with CFP that remained on the membrane (FIG. 2c, middle panel), and a short C-terminal fragment of SNAP-25 tagged with YFP that was expected to redistribute into the cytosol after toxin cleavage. Interestingly, we noticed the C-terminal cleavage product, SNAP-25(198-206)-YFP, largely disappeared after the toxin cleavage (FIG. 2c, the "YFP" frame in the middle panel). This observation was confirmed by immunoblot analysis (FIG. 7e), indicating this soluble fragment was degraded much faster than the other fragment that is retained on the membrane. This unexpected result provides an alternative way to detect toxin activity in living cells by simply monitoring the ratio between CFP and YFP fluorescence.

It was recently reported that the BoNT/A light chain contains membrane localization signals and targets to the plasma membrane in differentiated PC12 cells (Fernandez-Salas et al., Plasma membrane localization signals in the light chain of *botulinum* neurotoxin. Proc. Natl. Acad. Sci. USA 101, 3208-3213 (2004). Thus, we investigated the possibility that membrane anchoring of SNAP-25 is critical for efficient cleavage by BoNT/A. To directly test this idea, CFP-SNAP-25(Cys-Ala)-YFP, which was distributed in the cytosol (FIG. 7d), and CFP-SNAP-25(FL)-YFP, which was anchored to the plasma membrane, were used to transfect PC12 cells and assayed in parallel for the cleavage by BoNT/A in cells. As indicated in FIG. 7e, incubation of cells with BoNT/A resulted in the cleavage of significant amount of CFP-SNAP-25(FL)-YFP sensor, while there was no detectable cleavage of CFP-SNAP-25 (Cys-Ala)-YFP under the same assay conditions.

To further confirm this finding, we also targeted the inefficient sensor that contains SNAP-25(141-206) to the plasma membrane using a short fragment of SNAP-25 (residues 83-120, which can target GFP to plasma membranes (Gonzalo et al., SNAP-25 is targeted to the plasma membrane through a novel membrane-binding domain. J. Biol. Chem. 274, 21313-21318 (1999)) (FIG. 8a). As expected, anchoring of the CFP-SNAP-25(141-206)-YFP sensor to the plasma membrane resulted in efficient cleavage by BoNT/A (FIG. 8b). These findings indicate that the sub-cellular localization of SNAP-25 is indeed critical for the efficient cleavage by BoNT/A in cells.

Figure 9:
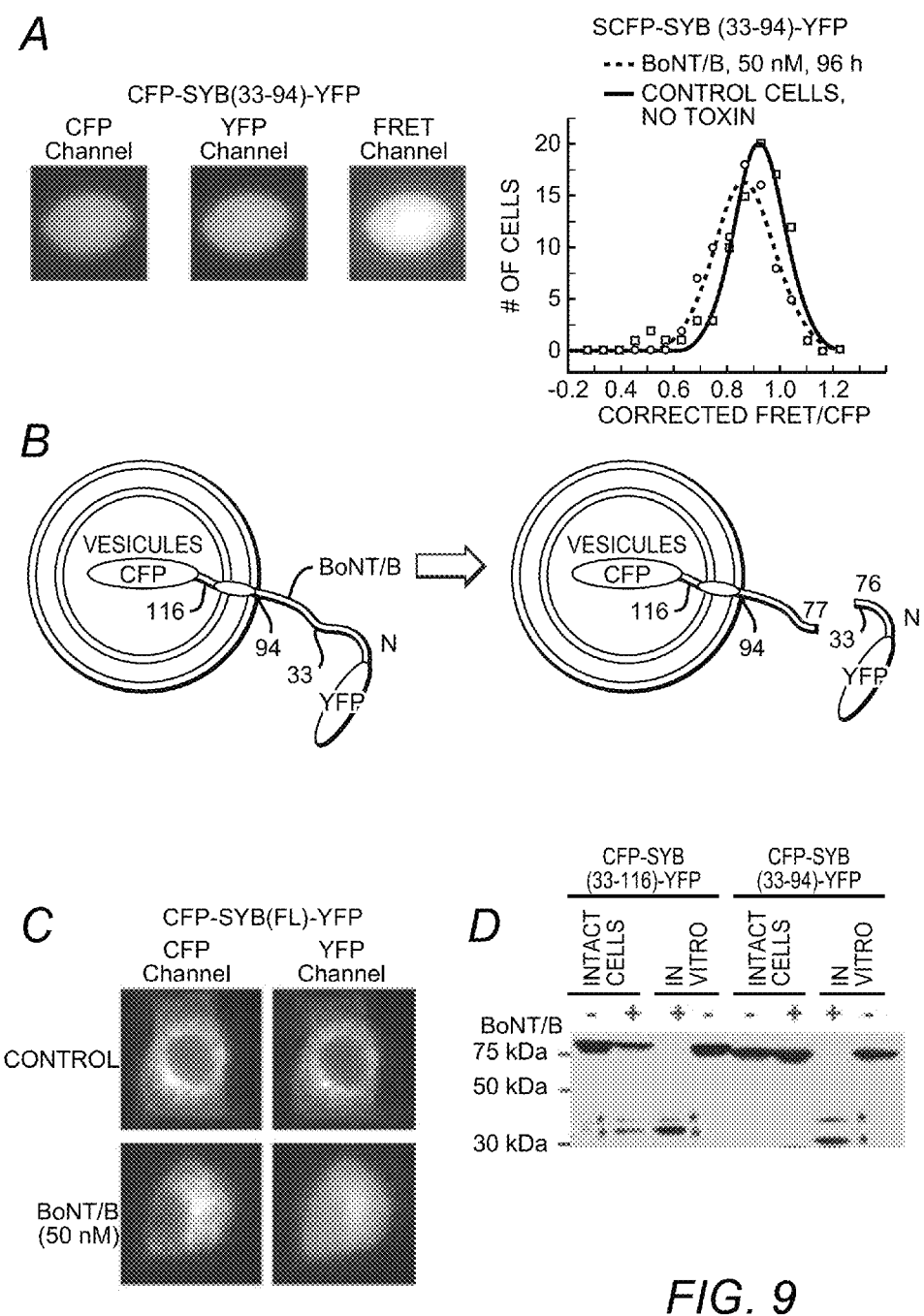
FIG. 9 shows that efficient cleavage of Syb by BoNT/B requires the localization of Syb to vesicles. (a). CFP-Syb(33-94)-YFP was used to transfect a PC12 cell line that stably expresses synaptotagmin II (Dong et al. Synaptotagmins I and II mediate entry of *botulinum* neurotoxin B into cells. J. Cell Biol. 162, 1293-1303 (2003)). This sensor appears to be soluble inside cells and generates strong FRET signals (upper panel). PC12 cells transfected with CFP-Syb(33-94)-YFP were used to detect BoNT/B activity. Fifty nM BoNT/B holotoxin was added to the culture medium and 80 cells were analyzed after 96 hours as described in FIG. 7b. Control cells were transfected with the same sensor but were not treated with toxins, and they were analyzed in parallel. Incubation with BoNT/B shifted the FRET ratio among the cell population, indicating the sensor proteins were cleaved by BoNT/B in cells. However, the shift was small, indicating that the cleavage was not efficient in cells. (b). A schematic description of YFP-Syb(FL)-CFP sensor. Full-length Syb contain 116 amino acids, and is localized to vesicles through a single transmembrane domain. Cleavage of Syb by BoNT/B released the cytoplasmic domain of Syb tagged with YFP from the vesicle. (c). PC12 cells that stably express synaptotagmin II were transfected with YFP-Syb(FL)-CFP, and were treated with BoNT/B (50 nM, 48 h, lower frames), or without toxin (control, upper frames). CFP and YFP fluorescence images were collected for each cell, and representative cells are shown. This sensor is localized to vesicles, and was excluded from the nucleus in living cells, as evidenced by both CFP and YFP fluorescent signals (upper frames). BoNT/B treatment resulted in a redistribution of YFP signals, which became soluble in the cytosol and entered the nucleus. (d). A truncated version of Syb, residues 33-116, was used to link a CFP and YFP. This construct contains the same cytosolic region (residues 33-94, panel (b)) as the Syb fragments in the soluble sensor CFP-Syb(33-96)-YFP, and it also contains the transmembrane domain of Syb. PC12 cells that express synaptotagmin II were transfected with CFP-Syb(33-116)-YFP and CFP-Syb(33-94)-YFP. Cells were then treated with (+, intact cells) or without (−, intact cells) BoNT/B (50 nM, 48 h), and were harvested. Half of the cell extracts from samples that were not exposed to BoNT/B were also incubated with (+, in vitro) or without (−, in vitro) reduced BoNT/B in vitro (200 nM, 30 min, 37.degree. C.). Two cleavage products are indicated by asterisks. The same amount of each sample (30.mu.g cell lysate) was loaded to one SDS-page gel and subjected to immunoblot analysis using an anti-GFP antibody. While CFP-Syb(33-116)-YFP underwent significant cleavage in intact cells, there was no detectable cleavage of CFP-Syb(33-94)-YFP, indicating the localization to vesicles is important for efficient cleavage by BoNT/B in living cells.

We next tested whether the CFP-Syb(33-94)-YFP sensor could be used to assay BoNT/B activity in cells. For these studies, we used a PC12 cell line that expresses synaptotagmin II, which mediates BoNT/B entry into cells (Dong et al. Synaptotagmins I and II mediate entry of *botulinum* neurotoxin B into cells. J. Cell Biol. 162, 1293-1303 (2003)). As shown in FIG. 9a(upper panel), transfected CFP-Syb(33-94)-YFP is a soluble protein present throughout the cells. Similar to the case of CFP-SNAP-25(141-206)-YFP, BoNT/B (50 nM, 96 hr) treatment only slightly decreased the FRET ratio (FIG. 9a, lower panel), indicating that the cleavage of this sensor is also inefficient in cells.

Our experience with the BoNT/A sensor prompted us to investigate whether the sub-cellular localization of Syb is important for cleavage of Syb by BoNT/B. Endogenous Syb is 116 amino acid residues long, and resides on secretory vesicles through a single transmembrane domain (residues 95-116, FIG. 9b). In order to ensure proper vesicular localization, we used full-length Syb as the linker between CFP and YFP. Because CFP is relatively resistant to the acidic environment in the vesicle lumen (Tsien, The green fluorescent protein. Annu Rev Biochem 67, 509-544 (1998), the CFP was fused to the C-terminus of Syb and is predicted to reside inside vesicles, while the YFP was fused to the N-terminus of Syb and faces the cytosol (FIG. 9b). This sensor is denoted as YFP-Syb(FL)-CFP. Since FRET is unlikely to occur between CFP and YFP here, a novel approach was taken to monitor the cleavage by BoNT/B. Cleavage of YFP-Syb(FL)-CFP sensor would generate two fragments, including a N-terminal portion tagged with YFP, which would be released into the cytosol, and a short C-terminal portion tagged with CFP that is restricted inside vesicles. Thus, toxin activity would result in the redistribution of YFP fluorescence in cells. YFP-Syb(FL)-CFP proved to be an efficient toxin sensor in cells. As indicated in FIG. 9c, treatment with BoNT/B resulted in the dissociation of YFP from the vesicles and its redistribution into the cytosol. We note that the soluble YFP fragment was able to enter the nucleus, where there was no fluorescence signal prior to toxin treatment (FIG. 9c), providing an area where the YFP redistribution can be readily detected. Unlike the FRET assay, this detection method does not require a short distance between CFP and YFP, thus providing a novel approach to monitor protease activity in living cells.

To exclude the possibility that the inefficient cleavage of the sensor containing Syb(33-94) fragment is due to the lack of the N-terminal 32 amino acid, a sensor containing the truncated form of Syb that lacks the N-terminal 32 residues (denoted as CFP-Syb(33-116)-YFP) was built. This sensor contains the same cytosolic domain of Syb with the inefficient sensor (residues 33-94), plus the transmembrane domain (residues 95-116), which anchors it to vesicles. When assayed in parallel, significant amount of CFP-Syb(33-116)-YFP was cleaved by BoNT/B after 48 hours, while there was no detectable cleavage of CFP-Syb(33-94)-YFP (FIG. 9d), indicating the vesicular localization determines the cleavage efficiency in cells. This conclusion is further supported by a recent report that the presence of negatively charged lipid mixtures enhanced the cleavage rate of Syb by BoNT/B, TeNT, and BoNT/F in vitro (Caccin et al., VAMP/synaptobrevin cleavage by tetanus and *botulinum* neurotoxins is strongly enhanced by acidic liposomes. FEBS Lett. 542, 132-136 (2003). It is possible that toxins may favor binding to vesicular membranes in cells, thus increasing the chance to encounter Syb localized on vesicles. Alternatively, it is also possible that the presence of the transmembrane domain may be critical for maintaining a proper conformational state of Syb that is required for efficient cleavage.

Using full length SNAP-25 and Syb II as the linkers provided excellent optical reporters that can mirror endogenous substrate cleavage in living cells. These two reporters should be able to detect all seven *botulinum* neurotoxins and tetanus neurotoxin (TeNT). The substrate linker sequence can be readily modified to achieve specific detection for individual BoNTs or TeNT by changing the length or mutating other toxin cleavage or recognition sites. These toxin biosensors should enable the cell-based screening of toxin inhibitors, and the study of toxin substrate recognition and cleavage in cells.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. All references cited hereinabove and/or listed below are hereby expressly incorporated by reference.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of improving sensitivity of energy transfer between a donor label and an acceptor label, comprising:
providing a first construct comprising the donor label and the acceptor label physically coupled through a linker, wherein the linker comprises an amino acid sequence at least 55 amino acids in length and comprising a cleavage site sequence and a flexible spacer sequence, wherein the spacer sequence is interposed between at least one of the group consisting of the donor label and the cleavage site and the acceptor label and the cleavage site;
contacting the first construct with a sample, wherein the sample comprises an activity directed to the cleavage site;
detecting a fluorescene emission from the first construct, thereby
characterizing an energy transfer between the donor label and the acceptor label,
wherein the energy transfer is enhanced relative to that of a second construct that does not include a spacer sequence.

2. The method of claim 1, wherein the construct is a protein-based construct, and the linker is a peptide sequence.

3. The method of claim 1, wherein the cleavage site sequence comprises a SNARE protein, or a fragment or mutein thereof, and wherein the spacer comprises at least five amino acids.

4. The method of claim 1, wherein the spacer includes a sequence selected from the group consisting of (GGGGS)n [Seq ID 7] and (EAAAK)n [Seq ID 8], where n is 1-3.

5. The method of claim 1, wherein the spacer increases the electronic coupling between the donor and the acceptor by reducing a tertiary structure distance between the donor and the acceptor.

6. The method of claim 1, wherein the spacer increases the electronic coupling between the donor and the acceptor by providing an electronic hop between the donor and the acceptor.

7. The method of claim 1, wherein an assay is applied to whole cells.

8. A method for detecting a *botulinum* neurotoxin, the method comprising, a) providing a construct comprising a donor label and an acceptor label physically coupled through a linker, wherein the linker comprises an amino acid sequence at least 55 amino acids in length and comprising a cleavage site sequence and a flexible spacer sequence, wherein the flexible spacer sequence is interposed between the cleavage site and at least one of the group consisting of the donor label and acceptor label, and wherein the cleavage site sequence is at least a cleavable portion of a substrate protein the *botulinum* neurotoxin to be detected, b) exposing the construct to a sample suspected of containing the *botulinum* neurotoxin under a condition under which the *botulinum* neurotoxin cleaves the cleavable portion of the substrate protein, and c) detecting and comparing a FRET signal before and after the construct is exposed to the sample, wherein a decrease in FRET indicates the presence of *botulinum* neurotoxin in the sample.

\* \* \* \* \*

SEQUENCE LISTING

```
<160> NUMBER OF SEQ ID NOS: 10

<210> SEQ ID NO 1
<211> LENGTH: 8
<212> TYPE: PRT
<213> ORGANISM: Artificial
<220> FEATURE:
<223> OTHER INFORMATION: Putative minimum recognition sequence BoNT/A

<400> SEQUENCE: 1

Glu Ala Asn Gln Arg Ala Thr Lys
1               5

<210> SEQ ID NO 2
<211> LENGTH: 8
<212> TYPE: PRT
<213> ORGANISM: Artificial
<220> FEATURE:
<223> OTHER INFORMATION: Putative minimum recognition sequence BoNT/B

<400> SEQUENCE: 2

Gly Ala Ser Gln Phe Glu Thr Ser
1               5

<210> SEQ ID NO 3
<211> LENGTH: 8
<212> TYPE: PRT
<213> ORGANISM: Artificial
<220> FEATURE:
```

```
<223> OTHER INFORMATION: Putative minimum recognition sequence BoNT/C
      (SNAP25)

<400> SEQUENCE: 3

Ala Asn Gln Arg Ala Thr Lys Met
1               5

<210> SEQ ID NO 4
<211> LENGTH: 8
<212> TYPE: PRT
<213> ORGANISM: Artificial
<220> FEATURE:
<223> OTHER INFORMATION: Putative minimum recognition sequence
      (syntaxin)

<400> SEQUENCE: 4

Asp Thr Lys Lys Ala Val Lys Phe
1               5

<210> SEQ ID NO 5
<211> LENGTH: 8
<212> TYPE: PRT
<213> ORGANISM: Artificial
<220> FEATURE:
<223> OTHER INFORMATION: Putative minimum recognition sequence BoNT/E

<400> SEQUENCE: 5

Gln Ile Asp Arg Ile Met Glu Lys
1               5

<210> SEQ ID NO 6
<211> LENGTH: 8
<212> TYPE: PRT
<213> ORGANISM: Artificial
<220> FEATURE:
<223> OTHER INFORMATION: Putative minimum recognition sequence BoNT/F

<400> SEQUENCE: 6

Glu Arg Asp Gln Lys Leu Ser Glu
1               5

<210> SEQ ID NO 7
<211> LENGTH: 5
<212> TYPE: PRT
<213> ORGANISM: Artificial
<220> FEATURE:
<223> OTHER INFORMATION: Synthetic linker (can be repeated between 1-3
      times, inclusive)

<400> SEQUENCE: 7

Gly Gly Gly Gly Ser
1               5

<210> SEQ ID NO 8
<211> LENGTH: 5
<212> TYPE: PRT
<213> ORGANISM: Artificial
<220> FEATURE:
<223> OTHER INFORMATION: Synthetic linker (can be repeated between 1-3
      times, inclusive)

<400> SEQUENCE: 8

Glu Ala Ala Ala Lys
1               5

<210> SEQ ID NO 9
<211> LENGTH: 10
```

```
<212> TYPE: PRT
<213> ORGANISM: Artificial
<220> FEATURE:
<223> OTHER INFORMATION: Synthetic substrate
<220> FEATURE:
<221> NAME/KEY: MISC_FEATURE
<222> LOCATION: (1)..(1)
<223> OTHER INFORMATION: CFP is covalently attached to amino group of
      serine
<220> FEATURE:
<221> NAME/KEY: MISC_FEATURE
<222> LOCATION: (7)..(8)
<223> OTHER INFORMATION: SNAP-15 is covalently inserted between alanine
      and serine
<220> FEATURE:
<221> NAME/KEY: MISC_FEATURE
<222> LOCATION: (10)..(10)
<223> OTHER INFORMATION: YFP is covalently attached to carboxylic acid
      group of serine

<400> SEQUENCE: 9

Ser Gly Leu Arg Ser Arg Ala Ser Asn Ser
1               5                   10

<210> SEQ ID NO 10
<211> LENGTH: 10
<212> TYPE: PRT
<213> ORGANISM: Artificial
<220> FEATURE:
<223> OTHER INFORMATION: Synthetic substrate
<220> FEATURE:
<221> NAME/KEY: MISC_FEATURE
<222> LOCATION: (1)..(1)
<223> OTHER INFORMATION: CFP is covalently attached to amino group of
      serine
<220> FEATURE:
<221> NAME/KEY: MISC_FEATURE
<222> LOCATION: (7)..(8)
<223> OTHER INFORMATION: Synaptobrevin is covalently inserted between
      alanine and serine
<220> FEATURE:
<221> NAME/KEY: MISC_FEATURE
<222> LOCATION: (10)..(10)
<223> OTHER INFORMATION: YFP is covalently attached to the carboxylic
      acid group of serine

<400> SEQUENCE: 10

Ser Gly Leu Arg Ser Arg Ala Ser Asn Ser
1               5                   10
```